(12) United States Patent
Isaacson et al.

(10) Patent No.: US 11,391,748 B2
(45) Date of Patent: Jul. 19, 2022

(54) HIGH DYNAMIC RANGE ASSAYS IN HAZARDOUS CONTAMINANT TESTING

(71) Applicant: Becton, Dickinson and Company, Franklin Lakes, NJ (US)

(72) Inventors: Ray Isaacson, Layton, UT (US); Brian Patrick Dwyer, San Diego, CA (US); Austin Jason Mckinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/134,003

(22) Filed: Sep. 18, 2018

(65) Prior Publication Data

US 2019/0086431 A1    Mar. 21, 2019

Related U.S. Application Data

(60) Provisional application No. 62/561,567, filed on Sep. 21, 2017.

(51) Int. Cl.
*G01N 33/94* (2006.01)
*G01N 33/543* (2006.01)

(52) U.S. Cl.
CPC ....... *G01N 33/94* (2013.01); *G01N 33/54386* (2013.01)

(58) Field of Classification Search
CPC .............................. G01N 33/543; G01N 33/00
USPC ......................................................... 436/524
See application file for complete search history.

(56) References Cited

U.S. PATENT DOCUMENTS

| 1,853,238 | A | 4/1932 | Shields |
| D229,689 | S | 12/1973 | Dragotta |
| 3,841,973 | A | 10/1974 | Wilkins et al. |
| 4,278,437 | A | 7/1981 | Haggar |
| 4,353,868 | A | 10/1982 | Joslin et al. |
| 4,707,450 | A | 11/1987 | Nason |
| 4,724,307 | A | 2/1988 | Dutton et al. |

(Continued)

FOREIGN PATENT DOCUMENTS

| CN | 107102103 A | 8/2017 |
| WO | WO 1995/25948 | 9/1995 |

(Continued)

OTHER PUBLICATIONS

Becton Dickinson—Veritor™ System—For Rapid Detection of Respiratory Syncytial Virus (RSV), Aug. 2017, Retrieved from the internet: <URL: https://www.bd.com/en-us/offerings/capabilities/microbiology-solutions/point-of-care-testing/veritor-system> in 16 pages.

(Continued)

*Primary Examiner* — Bao-Thuy L Nguyen
*Assistant Examiner* — Xiaoyan Zou
(74) *Attorney, Agent, or Firm* — Knobbe, Martens, Olson & Bear LLP

(57) ABSTRACT

Aspects of the disclosure relate to lateral flow assays having a number of different detection zones tuned to extend the dynamic range of the assay in indicating concentration of a hazardous contaminant in a test sample. Some aspects relate to assay reader devices configured with instructions to generate a result representing the concentration of the hazardous contaminant in the test sample based on some or all of the detection zones.

20 Claims, 15 Drawing Sheets

(56) References Cited

U.S. PATENT DOCUMENTS

| | | | |
|---|---|---|---|
| 4,956,302 | A | 9/1990 | Gordon et al. |
| 5,243,865 | A | 9/1993 | Hsu et al. |
| 5,373,748 | A | 12/1994 | Lioy et al. |
| 5,422,273 | A | 6/1995 | Garrison et al. |
| 5,511,654 | A | 4/1996 | de la Rocha |
| 5,511,934 | A | 4/1996 | Bracchi et al. |
| 5,543,115 | A | 8/1996 | Karakawa |
| D383,851 | S | 9/1997 | Wong |
| 5,798,273 | A | 8/1998 | Shuler et al. |
| 5,823,592 | A | 10/1998 | Kalidindi et al. |
| 5,888,758 | A | 3/1999 | Wu et al. |
| D425,625 | S | 5/2000 | Niermann |
| D438,979 | S | 2/2001 | Gomes et al. |
| 6,382,036 | B1 | 5/2002 | Woodmansee |
| 6,924,153 | B1 | 8/2005 | Boehringer et al. |
| D520,643 | S | 5/2006 | Clarke et al. |
| 7,114,403 | B2 | 10/2006 | Wu et al. |
| D558,357 | S | 12/2007 | Byrd et al. |
| D559,397 | S | 1/2008 | Eriksson et al. |
| D560,281 | S | 1/2008 | Kozak et al. |
| D574,507 | S | 8/2008 | Muir et al. |
| D594,131 | S | 6/2009 | Nguyen |
| 7,837,939 | B2 | 11/2010 | Tung et al. |
| D640,795 | S | 6/2011 | Jackson et al. |
| 8,128,871 | B2* | 3/2012 | Petruno ............ G01N 21/8483 422/68.1 |
| 8,486,717 | B2 | 7/2013 | O'Farrell et al. |
| D743,046 | S | 11/2015 | Poll et al. |
| D743,571 | S | 11/2015 | Jackson et al. |
| 9,488,585 | B2* | 11/2016 | Emeric ................ G01N 21/78 |
| 9,857,372 | B1 | 1/2018 | Pulitzer et al. |
| D859,683 | S | 9/2019 | Harding et al. |
| D882,817 | S | 4/2020 | Norton et al. |
| D898,220 | S | 10/2020 | Esala et al. |
| 10,916,058 | B2 | 2/2021 | Isaacson et al. |
| 11,002,642 | B2 | 5/2021 | Oshinski et al. |
| D923,195 | S | 6/2021 | Harding et al. |
| 2002/0001539 | A1 | 1/2002 | Dicesare et al. |
| 2002/0035869 | A1 | 3/2002 | Schroder et al. |
| 2003/0086074 | A1* | 5/2003 | Braig ............ A61B 5/150503 356/39 |
| 2004/0018634 | A1 | 1/2004 | Hajizadeh et al. |
| 2004/0248106 | A1 | 12/2004 | Leonard et al. |
| 2005/0084842 | A1 | 4/2005 | O'Connor |
| 2005/0106753 | A1 | 5/2005 | Wu et al. |
| 2005/0136540 | A1 | 6/2005 | Quine et al. |
| 2005/0136553 | A1 | 6/2005 | Kaylor et al. |
| 2005/0181517 | A1 | 8/2005 | Chandler et al. |
| 2005/0250141 | A1 | 11/2005 | Lambert et al. |
| 2006/0115805 | A1 | 6/2006 | Hansen et al. |
| 2006/0216196 | A1 | 9/2006 | Satoh et al. |
| 2007/0137319 | A1 | 6/2007 | Nacson et al. |
| 2007/0244368 | A1 | 10/2007 | Bayliff et al. |
| 2007/0276786 | A1 | 11/2007 | Piedmonte |
| 2008/0118397 | A1 | 5/2008 | Slowey et al. |
| 2009/0015273 | A1 | 1/2009 | Gossen et al. |
| 2009/0061534 | A1* | 3/2009 | Sharrock ............ G01N 33/545 436/518 |
| 2009/0223635 | A1 | 9/2009 | Lawless |
| 2010/0077843 | A1 | 4/2010 | Doraisamy et al. |
| 2011/0117025 | A1 | 5/2011 | Dacosta et al. |
| 2011/0201099 | A1 | 8/2011 | Anderson et al. |
| 2012/0011944 | A1 | 1/2012 | Maughan et al. |
| 2012/0044264 | A1 | 2/2012 | Lee et al. |
| 2012/0107956 | A1 | 5/2012 | Boehringer et al. |
| 2012/0264229 | A1 | 10/2012 | Wan |
| 2012/0282154 | A1 | 11/2012 | Slowey et al. |
| 2013/0253295 | A1 | 9/2013 | Tolosa et al. |
| 2013/0280143 | A1 | 10/2013 | Zucchelli et al. |
| 2014/0017812 | A1 | 1/2014 | Smith et al. |
| 2014/0080129 | A1 | 3/2014 | Klunder et al. |
| 2014/0121487 | A1 | 5/2014 | Faybishenko et al. |
| 2014/0176603 | A1 | 6/2014 | Kumar et al. |
| 2014/0183256 | A1 | 7/2014 | Calio et al. |
| 2014/0210857 | A1 | 7/2014 | Liu et al. |
| 2014/0309556 | A1 | 10/2014 | Fletcher et al. |
| 2015/0132795 | A1 | 5/2015 | Griswold et al. |
| 2015/0211987 | A1 | 7/2015 | Burg et al. |
| 2015/0241358 | A1 | 8/2015 | Burg et al. |
| 2015/0302662 | A1 | 10/2015 | Miller |
| 2016/0019716 | A1 | 1/2016 | Huang et al. |
| 2016/0041167 | A1 | 2/2016 | Campbell et al. |
| 2016/0057413 | A1 | 2/2016 | Zhou et al. |
| 2016/0077013 | A1 | 3/2016 | Attar et al. |
| 2016/0078680 | A1 | 3/2016 | Reif et al. |
| 2016/0258874 | A1 | 9/2016 | Truex |
| 2017/0016045 | A1 | 1/2017 | McDaniel |
| 2017/0072393 | A1 | 3/2017 | Jackson et al. |
| 2017/0153185 | A1 | 6/2017 | Kisner et al. |
| 2017/0154438 | A1 | 6/2017 | Kisner et al. |
| 2018/0247024 | A1 | 8/2018 | Divine et al. |
| 2018/0293350 | A1 | 10/2018 | Dimov et al. |
| 2018/0372595 | A1 | 12/2018 | Pais et al. |
| 2019/0035153 | A1 | 1/2019 | Dange |
| 2019/0086295 | A1 | 3/2019 | Oshinski et al. |
| 2019/0086296 | A1 | 3/2019 | West |
| 2019/0086305 | A1 | 3/2019 | Harding et al. |
| 2019/0086380 | A1 | 3/2019 | Harding et al. |
| 2019/0088026 | A1 | 3/2019 | Isaacson et al. |
| 2019/0120727 | A1 | 4/2019 | Harding et al. |
| 2020/0241020 | A1 | 7/2020 | Oshinski |
| 2020/0298240 | A1 | 9/2020 | Oshinski et al. |
| 2021/0192850 | A1 | 6/2021 | Isaacson et al. |
| 2021/0255066 | A1 | 8/2021 | Oshinski et al. |

FOREIGN PATENT DOCUMENTS

| | | |
|---|---|---|
| WO | WO 2009/018473 | 2/2009 |
| WO | WO 2010/001296 | 1/2010 |
| WO | WO 2011/095599 | 8/2011 |
| WO | WO 2013/036913 | 3/2013 |
| WO | WO 2014/015076 | 1/2014 |
| WO | WO 2014/025415 | 2/2014 |
| WO | WO 2015/187335 | 12/2015 |
| WO | WO 2016/040642 | 3/2016 |
| WO | WO 2016/078919 | 5/2016 |
| WO | WO 2016/090176 | 6/2016 |

OTHER PUBLICATIONS

International Search Report and Written Opinion dated Nov. 14, 2018 for Int'l App. No. PCT/US2018/051432.

Becton Dickinson—BD Diagnostics Preanalytical Systems—Product Catalogue 2014-15; 2013, Retrieved from internet: <URL:https://www.bd.com/be/dutch/pdfs/PAS_BNL_Prod_Cat_2014_2015_LR_Full_Catalogue.pdf> in 31 pages.

Becton Dickinson—BD HD Check Analyzer—Nursing Brochure; Mar. 2018, in 8 pages.

Becton Dickinson—BD HD Check Analyzer—Pharmacy Brochure; Mar. 2018, in 6 pages.

ChemoGlo, LLC, "ChemoGlo™—Detecting and Removing Hazardous Drugs"; available for download at https://web.archive.org/web/20150801115335/http://chemoglo.com/ at least as early as Aug. 1, 2015; 1 page.

ChemoGlo, LLC, ChemoGlo™ User Manual; available for download at https://web.archive.org/web/20150801115335/http://chemoglo.com/ at least as early as Aug. 1, 2015; 11 pages.

Preprocess, Inc., Sampling and Analytical Technique Considerations for Microbial Surface Swab Testing. 2015; Retrieved from the internet: <URL:http://www.preprocessinc.com/files/documents/d5840edf837f077be7b12e53494ed5b8.pdf> in 3 pages.

Technical Service Consultants Ltd., TS/15-T Product Specification Sheet; Issue #5 of Jun. 6, 2016; Retrieved from the Internet: URL: <http://www.tscswabs.co.uk/uploads/images/product-pdfs/product_specification/spec_TS15-T.pdf> in 20 pages.

De Keuckelaere et al., "Semi-Direct Lysis of Swabs and Evaluation of Their Efficiencies to Recover Human Noroviruses GI and GII from Surfaces", Food Environ Virol. (Jun. 2014) 6: 132-139.

Henderson S.J., "Augmented Reality Interfaces for Procedural Tasks", Doctoral Thesis; Columbia University, Apr. 14, 2011, 82 pages.

(56) References Cited

OTHER PUBLICATIONS

National Infection Service (England), Detection and enumeration of bacteria in swabs and other environmental samples. National Infection Service Food Water and Environmental Microbiology Standard Method, Sep. 1, 2017; 22 pages.

* cited by examiner

HIGH DYNAMIC RANGE ASSAYS IN HAZARDOUS CONTAMINANT TESTING

CROSS-REFERENCE TO RELATED APPLICATIONS

This application claims the benefit of U.S. Provisional Patent Application No. 62/561,567, filed on Sep. 21, 2017, entitled "HIGH DYNAMIC RANGE ASSAYS IN HAZARDOUS CONTAMINANT TESTING," the contents of which are hereby incorporated by reference herein.

TECHNICAL FIELD

The systems and methods disclosed herein are directed to environmental contaminant testing, and, more particularly, to a test device having increased dynamic range for identifying contaminant concentrations.

BACKGROUND

Antineoplastic drugs are used to treat cancer, and are most often found in a small molecule (like fluoruracil) or antibody format (like Rituximab). Detection of antineoplastic drugs is critical for determining if there is contamination/leakage in hospital/pharmacy areas where the drugs are used and/or dispensed.

The nature of antineoplastic drugs make them harmful to healthy cells and tissues as well as the cancerous cells. Precautions should be taken to eliminate or reduce occupational exposure to antineoplastic drugs for healthcare workers. Pharmacists who prepare these drugs and nurses who may prepare and administer them are the two occupational groups who have the highest potential exposure to antineoplastic agents. Additionally, physicians and operating room personnel may also be exposed through the treatment of patients, as patients treated with antineoplastic drugs can excrete these drugs. Hospital staff, such as shipping and receiving personnel, custodial workers, laundry workers and waste handlers, all have the potential to be exposed to these drugs during the course of their work. The increased use of antineoplastic agents in veterinary oncology also puts these workers at risk for exposure to these drugs.

SUMMARY

Antineoplastic drugs are antiproliferative as they affect the process of cell division by damaging DNA and initiating apoptosis, a form of programmed cell death. While this can be desirable for preventing development and spread of neoplastic (e.g., cancerous) cells, antineoplastic drugs can also affect rapidly dividing non-cancerous cells. As such, antineoplastic drugs can suppress healthy biological functions including bone marrow growth, healing, hair growth, and fertility, to name a few examples.

Studies have associated workplace exposures to antineoplastic drugs with health effects such as skin rashes, hair loss, infertility (temporary and permanent), effects on reproduction and the developing fetus in pregnant women, increased genotoxic effects (e.g., destructive effects on genetic material that can cause mutations), hearing impairment and cancer. These health risks are influenced by the extent of the exposure and the potency and toxicity of the hazardous drug. Although the potential therapeutic benefits of hazardous drugs may outweigh the risks of such side effects for ill patients, exposed health care workers risk these same side effects with no therapeutic benefit. Further, it is known that exposures to even very small concentrations of antineoplastic drugs may be hazardous for workers who handle them or work near them, and for known carcinogenic agents there is no safe level of exposure.

Environmental sampling can be used to determine the level of workplace contamination by antineoplastic agents. However, sampling and decontamination of contaminated areas is complicated by a lack of quick, inexpensive methods to first identify these areas and then determine the level of success of the decontamination. Although analytical methods are available for measuring antineoplastic drugs in environmental samples, these methods require shipment to outside labs, delaying the receipt of sampling results.

In one example sampling system suitable for use with the devices of the present disclosure, work surfaces can be sampled by providing the surface with a buffer solution and wiping the wetted surface with an absorbent swab, or by wiping the surface with a swab pre-wetted with the buffer solution. The buffer fluid can have properties that assist in picking up contaminants from the surface and releasing collected contaminants from swab material in some implementations, and mix the contamination into a homogeneous solution for testing. The buffer solution, together with any collected contaminants, can be expressed or extracted from the swab and this solution can be analyzed at the site of testing for presence and/or quantity of specific antineoplastic agents.

For example, the solution can be provided onto a competitive assay which can then be read by an assay reader device. Competitive assays may be desirable for detecting quantities of antineoplastic drugs due to the binding properties of these drugs, as explained in more detail below. With competitive assays, analytes (here, antineoplastic agents) in the sample compete with a signal-producing substance for a limited number of binding sites in a detection zone, such that increased presence of the antineoplastic agent causes less visible changes to the detection zone. When reading competitive assays, the relationship between the signal obtained by the reader device and the quantity of detected drug is modeled by an inverse curve. Thus, lower signals are correlated with higher quantities of detected drug and higher signals are correlated with lower quantities of detected drug. This inverse relationship curve creates difficulties in distinguishing between concentrations outside of a specific range of concentrations that can readily detected on a given test strip. In this range, referred to as the dynamic range of the test strip, detection zone saturation levels corresponding to varying concentrations can be accurately distinguished from one another. As such, while enabling rapid detection of antineoplastic agents at the site of testing, competitive assays may suffer from drawbacks relating to low dynamic range.

These and other problems are addressed in embodiments of the hazardous drug collection and detection systems described herein, which include competitive lateral flow assay test strips and associated reader devices that use multiple detection zones on a single test strip, for example each tuned to different levels of drug concentration, that can be used in combination to determine hazardous drug concentration in the liquid sample. The present technology provides improved sensitivity to a wider dynamic range of antineoplastic drug concentrations, including trace amounts of antineoplastic drugs, compared to existing systems. The detection system is capable of accurately detecting quantities of even trace amounts of antineoplastic agents and of providing results quickly (including immediately after collection). Advantageously, testing and detection can occur at the location of the collection so that immediate, quantitative assessment of contamination level can be determined without the delay required for laboratory sample processing.

Accordingly, one aspect relates to a system for detection of a hazardous contaminant, comprising an assay test strip including at least one material configured to wick a liquid sample containing the hazardous contaminant along a lateral flow path extending at least partway from a first end of the assay test strip to a second end of the assay test strip; a conjugate release zone comprising a plurality of diffusively bound labeled particles configured to be transported along the lateral flow path with the liquid sample; and a plurality of detection zones positioned sequentially along the lateral flow path, each of the plurality of detection zones comprising a plurality of immobilized capture reagents tuned to fully saturate with the labeled particles at a different one of a plurality of concentrations of the hazardous contaminant; and a reader device including a portion configured to receive the assay test strip; a sensor positioned to receive light reflected from the plurality of detection zones and configured to generate signals representing an intensity of the received light; and control electronics configured to analyze the signals, identify a subset of the plurality of detection zones saturated above a predetermined threshold, and determine a concentration of the hazardous contaminant in the liquid sample based on one of the subset of the plurality of detection zones.

In some embodiments of the system, the control electronics are configured to identify a highest concentration, from among a subset of the plurality of concentrations associated with the subset of the plurality of detection zones. In some further embodiments, the control electronics are configured to set the concentration of the hazardous contaminant in the liquid sample to the identified highest concentration associated with the subset of the plurality of concentrations. In some further embodiments, the plurality of detection zones are arranged along the lateral flow path in increasing order based on their tuned concentrations. In some further embodiments, the control electronics are configured to identify the highest concentration based on identifying a detection zone of the plurality of detection zones that is positioned farthest along the lateral flow path and saturated at least to a threshold level, and setting the highest concentration to the concentration of the plurality of concentrations of the identified detection zone. In some further embodiments, the control electronics are configured to output a confidence level in the concentration of the hazardous contaminant in the liquid sample.

In some embodiments of the system, the control electronics are configured to convert the concentration of the hazardous contaminant in the liquid sample to a measure of concentration of the hazardous contaminant of a tested area.

Some embodiments of the system further comprise a cartridge housing the assay test strip. In some further embodiments, the assay test strip comprises a sample receiving zone at the first end, and wherein the cartridge comprises a fluid fitting positioned to provide the liquid sample to the sample receiving zone. In some further embodiments, the fluid fitting is configured to provide a fluid-tight seal with a corresponding fluid fitting on a collection container for transferring the liquid sample from the collection container to the assay test strip. In some further embodiments, the cartridge comprises a machine-readable indication readable by the reader device to identify a number, location, and corresponding tuned concentration of each of the plurality of detection zones. In some further embodiments, the control electronics are further configured to identify the number, location, and corresponding tuned concentration of each of the plurality of detection zones based on signals from a barcode scanner representing the barcode.

In some embodiments of the system, the assay test strip comprises a competitive assay, and wherein each of the plurality of detection zones is configured to saturate in an inverse relationship with the concentration of the hazardous contaminant in the liquid sample.

Another aspect relates to a system for detection of a hazardous contaminant, comprising an assay test strip including at least one material configured to wick a liquid sample containing the hazardous contaminant along a lateral flow path extending at least partway from a first end of the assay test strip to a second end of the assay test strip; a conjugate release zone comprising a plurality of diffusively bound labeled particles configured to be transported along the lateral flow path with the liquid sample; and a plurality of detection zones positioned sequentially along the lateral flow path, each of the plurality of detection zones comprising a plurality of immobilized capture reagents tuned to fully saturate with the labeled particles at a specific concentration level of the hazardous contaminant; and a reader device including a portion configured to receive the assay test strip; a sensor positioned to receive light reflected from the plurality of detection zones and configured to generate signals representing an intensity of the received light; and control electronics configured to analyze the signals and determine a concentration of the hazardous contaminant in the liquid sample based on each of the plurality of detection zones.

In some embodiments of the system, the control electronics are configured to calculate, based on the signals, a saturation level of each of the plurality of detection zones; access data representing the concentration level associated with each of the plurality of detection zones; and calculate the concentration of the hazardous contaminant in the liquid sample based on the calculated saturation level and associated concentration level of each of the plurality of detection zones. In some further embodiments, the control electronics are configured to for each of the plurality of detection zones, generate a concentration product value by multiplying the calculated saturation level by the associated concentration level; and sum the concentration product values to calculate the concentration of the hazardous contaminant in the liquid sample.

In some embodiments of the system, the plurality of detection zones are each tuned to the same concentration.

In some embodiments of the system, the plurality of detection zones are each tuned to a different one of a plurality of concentrations. In some further embodiments, the plurality of detection zones are arranged along the lateral flow path in increasing order based on their tuned concentrations.

Some embodiments of the system further comprise a cartridge housing the assay test strip. In some further embodiments, the assay test strip comprises a sample receiving zone at the first end, and wherein the cartridge comprises a fluid fitting positioned to provide the liquid sample to the sample receiving zone. In some further embodiments, the fluid fitting is configured to provide a fluid-tight seal with a corresponding fluid fitting on a collection container for transferring the liquid sample from the collection container to the assay test strip. In some further embodiments, the cartridge comprises a barcode readable by the reader device to identify a number, location, and corresponding tuned concentration of each of the plurality of detection zones. In some further embodiments, the control electronics are further configured to identify the number, location, and corresponding tuned concentration of each of the plurality of detection zones based on signals from a barcode scanner representing the barcode.

In some embodiments of the system, the assay test strip comprises a competitive assay, and wherein each of the plurality of detection zones is configured to saturate in an inverse relationship with the concentration of the hazardous contaminant in the liquid sample.

Another aspect relates to a lateral flow assay comprising an assay test strip including at least one material configured to wick a liquid sample containing the hazardous contaminant along a lateral flow path extending from a first end of the assay test strip to a second end of the assay test strip; a sample receiving zone at the first end; a conjugate release zone positioned down the lateral flow path from the sample receiving zone and comprising a plurality of diffusively bound labeled particles configured to be transported along the lateral flow path with the liquid sample; and a plurality of detection zones positioned sequentially along the lateral flow path, each of the plurality of detection zones comprising a plurality of immobilized capture reagents tuned to fully saturate with the labeled particles at a specific concentration level of the hazardous contaminant; and a cartridge housing the assay test strip, the cartridge comprising a fluid fitting positioned to provide the liquid sample to the sample receiving zone.

In some embodiments of the lateral flow assay, the plurality of detection zones are each tuned to the same concentration.

In some embodiments of the lateral flow assay, the plurality of detection zones are each tuned to a different one of a plurality of concentrations. In some further embodiments, the plurality of detection zones are arranged along the lateral flow path in increasing order based on their tuned concentrations.

Some embodiments of the lateral flow assay further comprise a control zone configured to saturate regardless of concentration level of the hazardous contaminant in the liquid sample.

In some embodiments of the lateral flow assay, the assay test strip comprises a competitive assay.

Another aspect relates to an assay reader device comprising a port configured to receive an assay test strip having a plurality of detection zones positioned sequentially along a lateral flow path, each of the plurality of detection zones comprising a plurality of immobilized capture reagents tuned to fully saturate with labeled particles at a specific concentration level of a hazardous contaminant; a sensor positioned to receive light reflected from the plurality of detection zones and configured to generate signals representing an intensity of the received light; and control electronics configured to analyze the signals and determine a concentration of the hazardous contaminant in the liquid sample based on at least some of the plurality of detection zones.

In some embodiments of the assay reader device, the plurality of detection zones are each tuned to a different one of a plurality of concentrations, and wherein the control electronics are configured to identify a highest concentration, from among a subset of the plurality of concentrations associated with the subset of the plurality of detection zones. In some further embodiments, the control electronics are configured to set the concentration of the hazardous contaminant in the liquid sample to the identified highest concentration associated with the subset of the plurality of concentrations.

In some embodiments of the assay reader device, the control electronics are configured to calculate, based on the signals, a saturation level of each of the plurality of detection zones; access data representing the concentration level associated with each of the plurality of detection zones; and calculate the concentration of the hazardous contaminant in the liquid sample based on the calculated saturation level and associated concentration level of each of the plurality of detection zones. In some further embodiments, the control electronics are configured to for each of the plurality of detection zones, generate a concentration product value by multiplying the calculated saturation level by the associated concentration level; and sum the concentration product values to calculate the concentration of the hazardous contaminant in the liquid sample.

Some embodiments of the assay reader device further comprise a barcode scanner positioned to read a barcode on a cartridge housing the assay test strip. In some further embodiments, the control electronics are further configured to identify, based on signals from the barcode scanner representing a scanned barcode, a number, location, and corresponding tuned concentration of each of the plurality of detection zones.

In some embodiments of the assay reader device, the control electronics are further configured to identify a value representing a level of confidence in accuracy of the determined concentration of the hazardous contaminant in the liquid sample, wherein the value is based on a difference between the concentration of the hazardous contaminant in the liquid sample and a predetermined threshold. Some further embodiments further comprise a display configured to display information representing the determined concentration of the hazardous contaminant in the liquid sample, and the control electronics are configured to cause output of a visual indication of the confidence value to the display.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

Figure 1A:
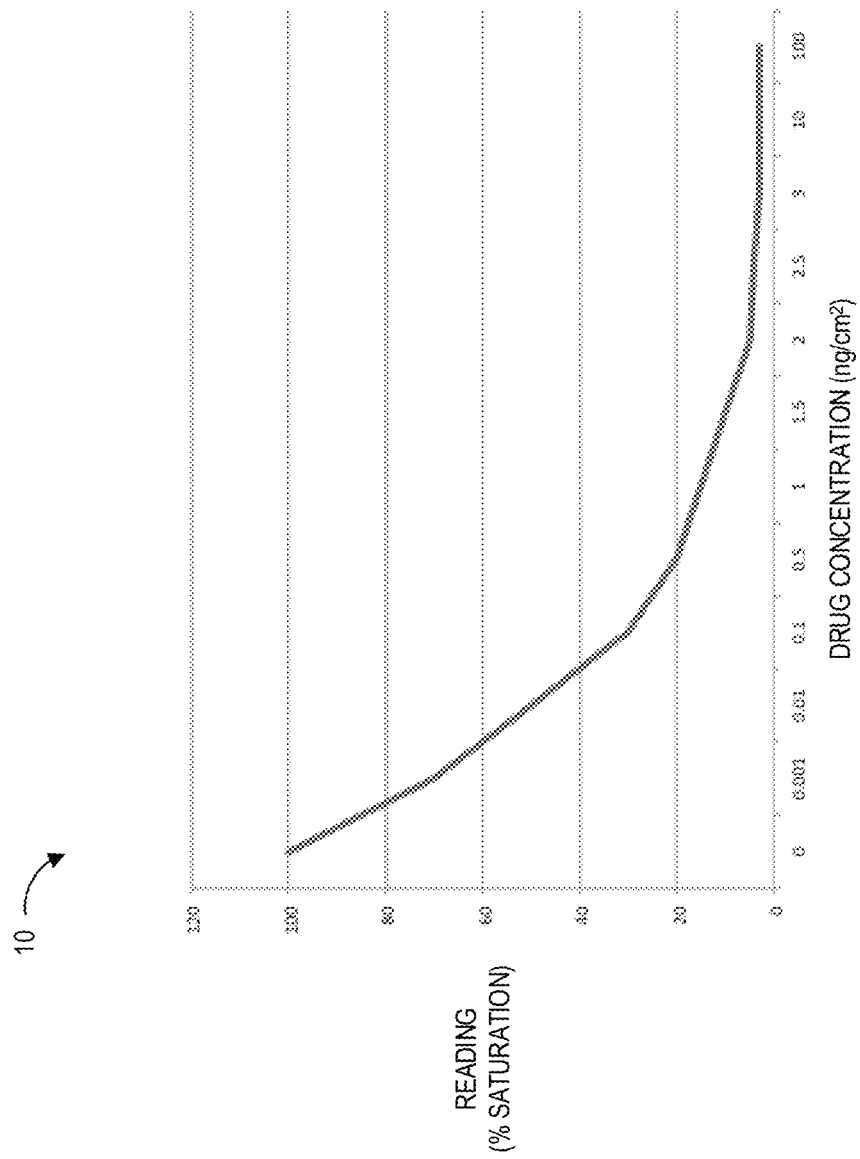
FIG. 1A illustrates an example plot of reading signal saturation for different antineoplastic drug concentrations.

Embodiments of the disclosure relate to systems and techniques for detection of hazardous environmental contaminants, such as but not limited to antineoplastic drugs used in the treatment of cancer, with increased sensitivity to trace concentrations of antineoplastic drugs in collected samples. A kit for such testing can include a collection device and a testing device. Throughout this disclosure, example systems, kits, and methods will be described with reference to collection, testing, and detection of antineoplastic agents, but it will be understood that the present technology can be used to collect, test, and detect any particle, molecule, or analyte of interest. In addition, signals generated by assays according to the present disclosure are described herein in the context of an optical signal generated by, for example, reflectance-type labels (such as but not limited to gold nanoparticle labels). Although embodiments of the present disclosure are described herein by reference to an "optical" signal, it will be understood that assays described herein can use any appropriate material for a label in order to generate a detectable signal, including but not limited to fluorescence-type latex bead labels that generate fluorescence signals and magnetic nanoparticle labels that generate signals indicating a change in magnetic fields associated with the assay.

Drugs successfully treat many types of illnesses and injuries, but virtually all drugs have side effects associated with their use. Not all adverse side effects classify as hazardous, however. In the present disclosure, the term "hazardous drugs" is used according to the meaning adopted by the American Society of Health-System Pharmacists (ASHP), which refers to a drug as hazardous if studies in animals or humans have indicated that exposures to them have any one of four characteristics: genotoxicity; carcinogenicity; teratogenicity or fertility impairment; and serious organ damage or other toxic manifestation at low doses in experimental animals or treated patients.

Although described in the example context of ascertaining the concentration of hazardous drugs such as antineoplastic agents, it will be appreciated that the disclosed test strips and reading techniques for extending competitive assay dynamic range can be used to detect the presence and/or concentration of any analyte of interest. An analyte generally refers to a substance to be detected. Analytes can include, for example, drugs (both hazardous and non-hazardous), antigenic substances, antibodies, proteins, haptens, nucleic acids and amplicons.

As used herein, "tuning" refers to selecting parameters of a test strip to achieve sensitivity to a desired concentration or range of concentrations. For example, the capture reagent loading concentration of a detection zone can be tuned so that the detection zone fully saturates at a desired level of contaminant concentration in the liquid sample. As another example, properties of the capture reagent can be tuned so that selective binding occurs in a manner that fully saturates a detection zone at a desired level of contaminant concentration in the liquid sample. As another example, properties of labeled conjugates can be tuned in order to produce full saturation of a detection zone at a desired level of contaminant concentration in the liquid sample. These and other tuning parameters can be modified in isolation or in combination in order to achieve the desired sensitivity of various detection zones as described herein.

The term "binding" refers to a physical or chemical interaction between two complementary molecules, for example an antineoplastic molecule and a labeled conjugate, an antineoplastic molecule and a capture reagent, a labeled conjugate and a capture reagent, and a control substance and a control reagent. Binding includes, but is not limited to, ionic bonding, non-ionic bonding, covalent bonding, hydrogen bonding, hydrophobic interaction, hydrophilic interaction, and Van der Waals interaction.

Though the disclosed detection zones are described in the context of competitive assays, it will be appreciated that the tuning principles described herein can be extended to other types of lateral flow assays, for example sandwich lateral flow assays. For example, at very high analyte concentrations the detection conjugate of a sandwich lateral flow assay becomes saturated and the excess analyte competes with the analyte-conjugate complex for capture antibody in the detection zone. This results in a decreasing signal (referred to as the hook effect). Providing multiple detection lines as described herein may help to mitigate this effect.

Various embodiments will be described below in conjunction with the drawings for purposes of illustration. It should be appreciated that many other implementations of the disclosed concepts are possible, and various advantages can be achieved with the disclosed implementations.

Introduction to Competitive Assays

Aspects of the present disclosure relate to techniques for enhancing the dynamic range of competitive assays for antineoplastic drug quantity detection by using multiple test zones on a single test strip. Example systems, kits, and methods are described throughout this disclosure with reference to collection, testing, and detection of antineoplastic drugs, but it will be understood that the present technology can be used to collect, test, and detect any particle, molecule, or analyte of interest. Competitive assays are a type of lateral flow assay that can be used when performing a test for certain types of analytes, including analytes of low molecular weight, a single antigenic determinant, and/or having one epitope only. Such analytes may not be able to bind to two antibodies simultaneously, as required by other forms of assays (e.g., sandwich assays). Some antineoplastic molecules have molecular weights and/or single epitopes, making them suitable for detection using competitive assays. As used herein, an antineoplastic molecule refers to one molecule of an antineoplastic drug. Competitive format assays described herein will be described in the context of reflective-type labels (such as gold nanoparticle labels) generating an optical signal, but it will be understood that assays may include latex bead labels configured to generate fluorescence signals, magnetic nanoparticle labels configured to generate magnetic signals, or any other label configured to generate a detectable signal.

In the disclosed competitive assays, antineoplastic molecules in the liquid sample compete with a signal-producing substance for a limited number of binding sites in a detection zone. As shown in the example plot 10 of FIG. 1A, the signal intensity read from a single detection zone of a competitive assay is in an inverse relationship with the concentration of analyte present. The plot 10 shows signal reading values, depicted as percentage of saturation (e.g., color intensity) of the test zone over a range of antineoplastic drug concentrations in the liquid sample, shown in nanograms per centimeter squared ($ng/cm^2$). As illustrated, a sample with no antineoplastic drug will yield a maximum signal intensity, and a sample with a range of antineoplastic drug concentrations will yield less than a maximum signal.

However, as also shown in FIG. 1A, this inverse relationship curve begins to create some difficulty in ascertaining concentration when the test zone saturation is low. For example, the saturation level varies little between 2 ng/cm$^2$ and 100 ng/cm$^2$, creating difficulty in ascertaining whether the liquid sample contains 2 ng/cm$^2$ antineoplastic drug concentration, 100 ng/cm$^2$ antineoplastic drug concentration, or somewhere in between. The liquid volume used to collect the sample can be increased or decreased, or the detection zone can be tuned to a different curve, however these approaches merely shift the illustrated curve left or right. Shifting the curve to the right can allow for better detection at higher concentrations, however the test strip would lose fidelity in detecting lower concentrations. Conversely, shifting the curve to the left can allow for better detection at lower concentrations, however the test strip would lose fidelity in higher lower concentrations. The range of concentrations that can be accurately determined based on a particular tuning curve is referred to as the "dynamic range" of the test strip.

Figure 1B:
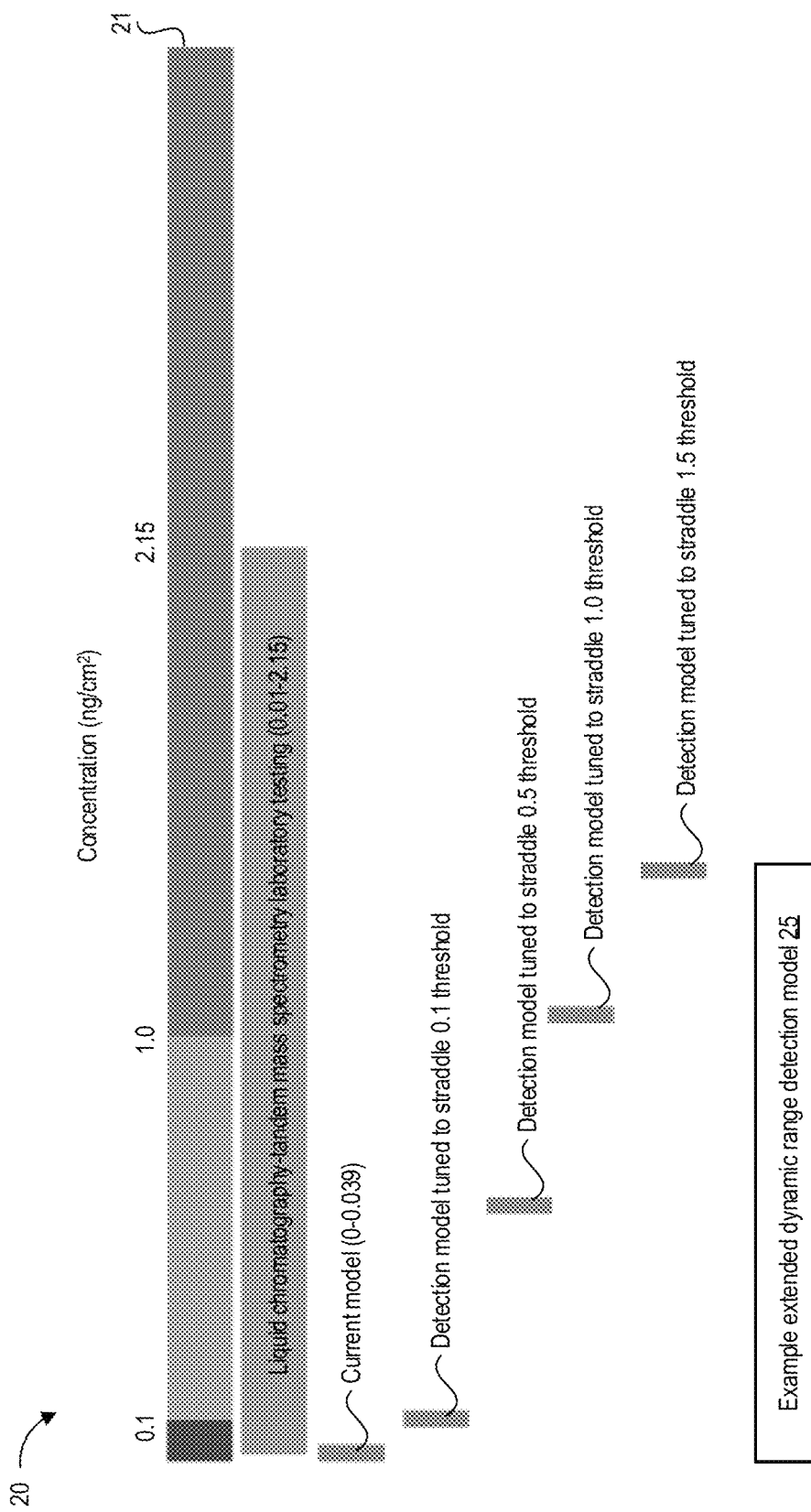
FIG. 1B illustrates an example model showing different levels of contamination that can be detected by different detection methods.

FIG. 1B illustrates an example model showing different levels of contamination that can be detected by different detection models, including competitive assays yielding inverse relationship curves as described with respect to FIG. 1A. The colored bar 21 shows the severity of different levels of contamination (in nanograms per centimeter squared, ng/cm$^2$) based on potential human uptake. A range between 0 ng/cm$^2$ and 0.1 ng/cm$^2$ is shown in blue, representing a range of least dangerous levels of contamination for humans. A range between 0.1 ng/cm$^2$ and 1.0 ng/cm$^2$ is shown in yellow, representing a range of moderately dangerous levels of contamination for humans. A range above 1.0 ng/cm$^2$ is shown in orange, representing a range of most dangerous levels of contamination for humans (though described as "most dangerous," this is relative to the two lower ranges, it will be appreciated that levels higher than the depicted orange bar can be even more dangerous for exposed humans).

Below the colored bar 21, FIG. 1B shows a graphical representation of the ranges of contamination levels that can be detected by various test devices. As illustrated, liquid chromatography-tandem mass spectrometry testing (shown by the light blue bar) performed in a laboratory can detect a range of contamination levels approximately between 0.01 ng/cm$^2$ and 2.15 ng/cm$^2$. However, this laboratory testing (as used in current antineoplastic contamination detection practices) requires a wait time of at least 4-6 weeks after the laboratory has received a sample wipe for a user to receive test results. The equipment required to perform such testing is expensive and complex, and as such is typically found in specialized testing laboratories and not in clinics, pharmacies, and other settings where neoplastic drugs are stored, dispensed, and provided as treatment to cancer patients.

The small green bars of FIG. 1B show the ranges afforded by lateral flow assays, for example competitive assays, having detection zones formulated according to varying detection models. Lateral flow assays provide advantages over the described laboratory testing because they can be used immediately after testing and at the site of testing, thus providing rapid feedback regarding detected concentration levels to the testing user and enabling them to take preventative actions (quarantining, decontamination procedures) that mitigate continued dangerous exposure of users in the test area to antineoplastic drugs. Some implementations of systems and methods according to the present disclosure provide a range from around 0.03 ng/cm$^2$ to 0.15 ng/cm$^2$. As depicted by the visual comparison of this range to the colored bar 21, this current model is only able to discern between the least dangerous contamination level and higher levels. This model cannot distinguish between the moderately and severely dangerous contamination levels. As such, a user testing a contaminated area with a concentration level above of 0.1 ng/cm$^2$ may not be able to ascertain from the test strip how contaminated the area actually is.

Further example models are shown that straddle the 0.1 ng/cm$^2$ threshold between the least dangerous and moderately dangerous ranges, the 0.5 ng/cm$^2$ threshold in the center of the moderately dangerous range, the 1.0 ng/cm$^2$ threshold between the moderately dangerous and most dangerous ranges, and the 1.5 ng/cm$^2$ threshold in the most dangerous range. Each of these models may be implemented in a competitive assay test strip, and thus provides the benefit of providing test results more rapidly than laboratory testing. However, each of these detection models may "miss" contamination levels below the corresponding green bar by outputting a negative result, and is not able to provide indication of contamination levels above the corresponding green bar. In order to detect a continuous, larger range, many such test strips would be required to test a single sample, thereby increasing the cost, time, and waste of testing.

Accordingly, in order to solve these problems, among others, FIG. 1B shows an example extended dynamic range of a detection model 25 implemented in a competitive assay according to the present disclosure. The illustrated detection model 25 can have a range from around 0 ng/cm$^2$ or 0.01 ng/cm$^2$ to around 1.5 ng/cm$^2$. As such, an assay formulated based on this detection model 25 can both output rapid results at the site and time of testing, as well as provide accurate indications of concentration levels across a wide range spanning all three of the least dangerous, moderately dangerous, and most dangerous contamination levels. Other embodiments can expand the range even further, as desired based on the contamination levels of interest for various antineoplastic agents. In addition, the dynamic range of assays described in the present disclosure can be adjusted based on the particular analyte of interest, the intended location of testing, and other factors. For example, the detection model 25 can be shifted to the right to detect higher concentrations (and not detect concentrations in the range of 0 ng/cm$^2$ or 0.1 ng/cm$^2$). In addition or alternatively, the dynamic range of the detection model 25 can be widened to measure a broader range of concentrations (for example, to detect concentrations in the range of 0 ng/cm$^2$ to 2.5 ng/cm$^2$). It will be understood that competitive assays described herein are not limited to these examples, and can be adjusted, given the particular environmental factors, analyte of interest, and user testing needs, to achieve any suitable dynamic range.

The present competitive assays, for example but not limited to an assay implementing the detection model 25, overcome the limited dynamic range of conventional competitive assays by employing a number of spatially distinct detection zones in combination with precise, automated reading techniques in order to identify a total concentration of hazardous drug in a liquid sample. In some implementations, each detection zone can be tuned to a different level of drug concentration. In some implementations, the saturation level of each detection zone can be compared to a threshold, and the concentration levels of sufficiently saturated detection zones can be combined to identify the total concentration of hazardous drug in the liquid sample. In some implementations, the saturation levels and fully saturated concentration levels of the various detection zones can be used in combination to identify the total concentration of hazardous drug in the liquid sample. An assay reader device can be provided with computer-executable instructions to optically obtain signals representing the various detection zones and to compute a total detected concentration level based on the strengths or intensities of these signals.

Some examples can be implemented as a binary test system, for example outputting positive or negative test results, rather than a quantitative system that communicates a specific contamination concentration to the user. For example, the reader device can output a + or − sign together with other test result information, such as outputting "DOXORUBICIN+" to indicate a positive test result for Doxorubicin or "DOXORUBICIN −" to indicate a negative test result for Doxorubicin. Implementations that output a qualitative test result can be particularly advantageous in scenarios where the degree of confidence that a contaminant is or is not present is very high with respect to a particular contamination concentration. To illustrate with one non-limiting example of system described herein, surfaces with contamination greater than 0.1 $ng/cm^2$ DOXORUBICIN are greater than 99% likely to read as positive and uncontaminated surfaces (0.0 $ng/cm^2$ DOXORUBICIN) are greater than 99% likely to read as negative. In this example, a quantitative system can output, with a high degree of confidence, a test result of "YES" or "DOXORUBICIN+" when the system detects a concentration of 0.1 $ng/cm^2$ or greater, and output a test result of "NO" or "DOXORUBICIN −" when the system detects a concentration of 0.0 $ng/cm^2$. The user could be instructed to perform a second test (for example, apply the collected sample to a second, unused assay test device) or be given a positive test result for contamination readings between 0.0 $ng/cm^2$ and 0.1 $ng/cm^2$. As demonstrated in this example, qualitative systems according to the present disclosure are capable of providing extremely useful information to the user at the test location immediately after the test event (in some cases within 1-10 minutes), even without displaying an indication of a detected contaminant concentration.

In some embodiments, the reader device (or instructions for use of the reader device) can correlate a positive or negative test result with a detected contaminant quantity and provide this information to the user. In one non-limiting example, the system outputs a binary result (yes/no; + or −) together with an indication of a contamination threshold or zone to which the binary result relates. The indication can be displayed to the user in any suitable manner, including but not limited to in instructions for use, in printed format on a physical template applied to the test surface, and in an augmented reality display. In one example, the user is provided information to correlate a test result of "−" to an indication that the tested surface is in the no-hazard or least hazardous contamination range (for example, inside the dark blue zone shown in FIG. 1B). In another example, the user is provided information to correlate a test result of "−" to an indication that the tested surface is in a slightly higher contamination range (for example, in a range that is straddling the 0.1 $ng/cm^2$ threshold shown in FIG. 1B). Additional features of embodiments of systems with at least one detection model tuned to straddle the 0.1 $ng/cm^2$ threshold are described in detail below. In still another example, the user is provided information to correlate a test result of "+" to an indication that the tested surface is in a very high contamination range (for example, in a range that is straddling the 1.5 $ng/cm^2$ threshold shown in FIG. 1B). Additional features of embodiments of systems with at least one detection model tuned to straddle the 1.5 $ng/cm^2$ threshold are described in detail below.

Figure 2:
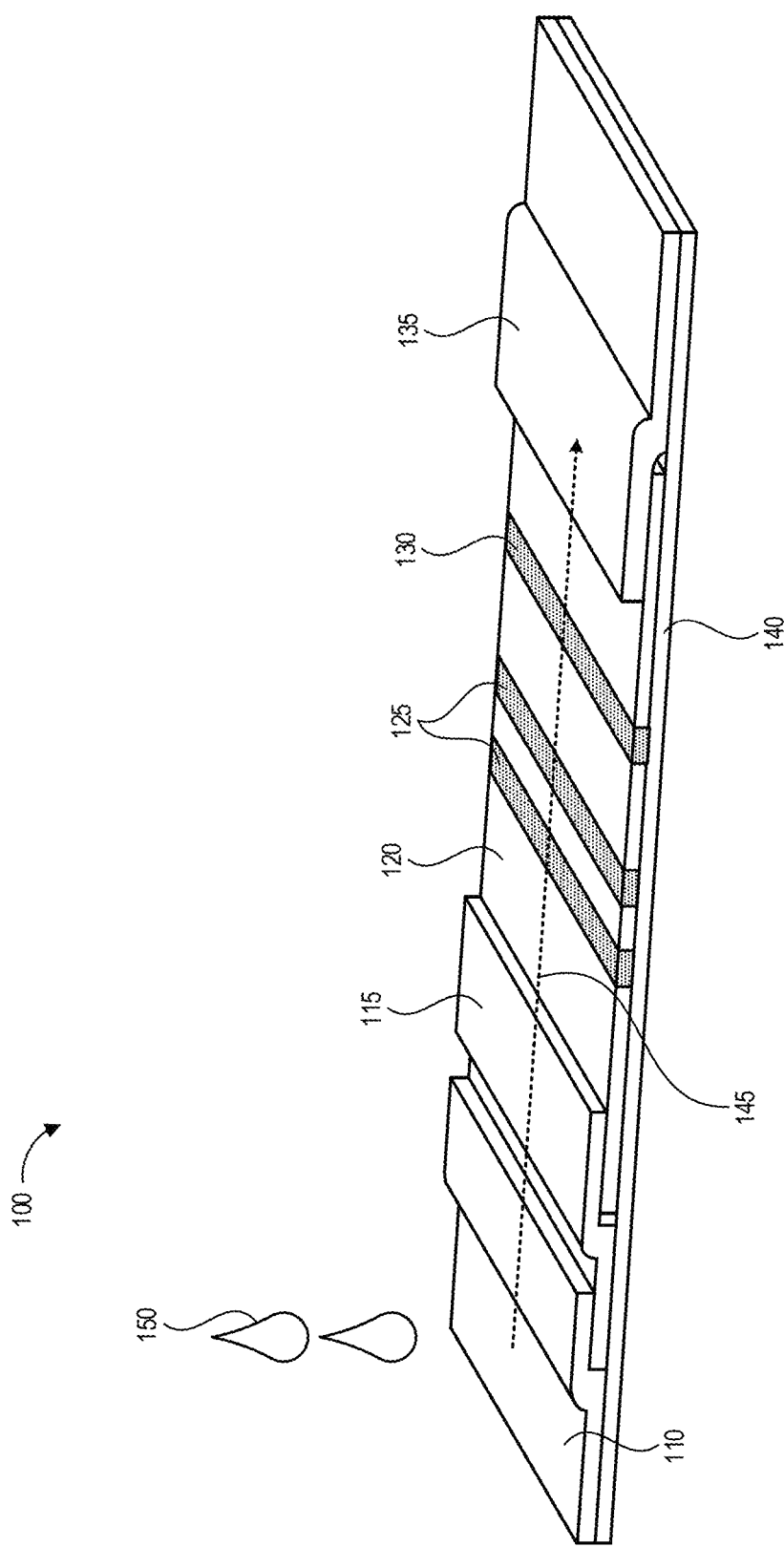
FIG. 2 illustrates a high-level diagram of an example competitive assay as described herein.

As shown in FIG. 2, a competitive assay test strip 100 as described herein can be formed from a substrate 120 including at least the following zones: a sample receiving zone 110, a conjugate release zone 115, a plurality of successive, spatially distinct detection zones 125, a control zone 130, and an adsorbent or absorbent zone 135. A liquid sample 150 collected from a potentially contaminated area moves via capillary action along a lateral flow path 145 of the substrate through the various zones of the test strip, to which molecules that can interact with the analyte are attached. Though illustrated as a line, it will be appreciated that the flow path 145 can extend across some or all of the width of the test strip 100.

The substrate 120 comprises at least one material configured to facilitate lateral flow 145 of the liquid sample 150 to wick the sample from one end of the test strip to the other. One example suitable material for the substrate 120 is a porous material, for example nitrocellulose. Some implementations can use a nonporous material formed as channels, for example micropillar arrays, to provide capillary action for the lateral flow 145. The various zones of the test strip 100 can be formed as part of the substrate 120 or as separate materials fluidically connected with one another and/or the substrate, e.g. capable of transmitting the lateral flow 145 of a liquid sample 150. Optionally the substrate 120 and the material of any zones that are not part of the substrate 120 can be secured to a support member 140, for example a rigid, planar structure formed from paper, metal, glass, plastic, or other suitable materials.

The liquid sample 150 is applied at the sample receiving zone 110 at one end of the test strip 100. The sample receiving zone 110 can evenly distribute the sample and to direct it to the conjugate release zone. The sample receiving zone 110 can comprise a portion of the substrate 120 or, as illustrated, can be a separate pad formed from the same or a different material as the substrate. The sample receiving zone 110 can optionally include compounds (e.g., buffer salts, surfactants, proteins, etc.) that facilitate interaction between the liquid sample 150 and the molecules in other zones.

The liquid sample 150 flows from the sample receiving zone 110 to and through the conjugate release zone 115. The conjugate release zone 115 contains diffusibly bound molecules that are conjugated to colored or fluorescent label particles (referred to herein as "labeled conjugate"). Label particles can be, for example, colored dye, colloidal gold, latex (e.g., microspheres), carbon, or fluorescent labels, to name a few. The term "diffusibly bound" as used herein refers to reversible attachment or adsorption of the labeled conjugate to the conjugate release zone such that the material moves with the lateral flow when contacted with the liquid sample. The conjugate release zone 115 is configured to release the labeled conjugate upon contact with the moving liquid sample. The conjugate release zone 115 can comprise a portion of the substrate 120 or, as illustrated, can be a separate pad formed from the same or a different material as the substrate. Suitable materials include glass fiber, cellulose, and polyesters, to name a few examples. The conjugate release zone 115 can also include a conjugate buffer to hold the labeled conjugate particles and keep them functionally stable until the test is performed. In one example, the conjugate buffer can contain carbohydrates (such as sucrose) that serve as a preservative and a resolubilization agent. When the labeled conjugate particles are dried in the presence of carbohydrates, the carbohydrate molecules form a layer around them, stabilizing their biological structures. When the liquid sample 150 enters the conjugate release zone 115, the carbohydrate molecules rapidly dissolve, carrying the labeled conjugate into the lateral flow path 145.

The liquid sample 150 and labeled conjugate are carried along the lateral flow path 145 from the conjugate release zone 115 to the successive detection zones 125. Although two detection zones 125 are illustrated, the disclosed test strips can have two, three, or more detection zones 125. Each detection zone 125 can comprise a region of the substrate 120 or a porous membrane coupled to the substrate 120, for example nitrocellulose. Each detection zone 125 has non-diffusibly bound capture reagents immobilized within the zone. The term "non-diffusibly bound" as used herein refers to attachment of the capture reagents to the material of the detection zone such that the capture reagent is immobilized and therefore does not move with the lateral flow when contacted with the liquid sample. Thus, the term "detection zone" refers to a region of the test strip where a capture reagent is non-diffusibly bound. A capture reagent can be any molecule that is complementary to and thus specifically binds with the labeled conjugate and/or an antineoplastic molecule. A detection zone 125 may have any of various shapes and sizes configured to allow for determination of binding of an analyte to the capture reagent. For example, a detection zone can include a line of non-diffusibly bound capture reagent, referred to as a "test line." The appearance of the test line can be used to determine a positive or negative result, or a quantity, for the analyte tested. Examples of the detection zones are described in further detail with reference to FIGS. 4A-4C.

In one implementation of a competitive assay, the labeled conjugate can be analogous to the target antineoplastic molecule, and both the labeled conjugate and target antineoplastic molecule can be complementary to the capture reagent. As used herein, complementary refers to two molecules of a binding pair having portions on their surfaces or in cavities that bind to one another. As the liquid sample flows through the conjugate release zone, the labeled conjugate is hydrated and released into the flowing liquid. Thus, as the liquid sample flows across the detection zones carrying with it the antineoplastic molecules (or other analyte of interest) and labeled conjugate, these molecules compete with each other to bind to a fixed amount of capture reagent in the detection zones. The labeled conjugate will bind to the capture reagents in the absence of the antineoplastic molecules, thus producing a saturation proportional to the quantity of labeled conjugate immobilized within the detection zone. When there is no antineoplastic molecule of interest in the sample, the labeled conjugate binds to all (or most) capture reagent sites within the detection zones, generating a saturation of maximum intensity. When an antineoplastic molecule of interest is present in the sample in low concentrations, the labeled conjugate competes with a relatively low amount of unlabeled antineoplastic molecules to bind to the capture reagent, resulting in a saturation that is the same as or substantially equivalent to (within a limited range of variance from) the maximum intensity. When antineoplastic molecules of interest are present in the sample in high concentrations, the labeled conjugate competes with a relatively high amount of unlabeled antineoplastic molecules to bind to the capture reagent, resulting in a signal that is less than the maximum intensity signal. In one non-limiting embodiment, the test strip can be structured so that the target antineoplastic molecule reaches the detection zones first and thus has the first opportunity to bind with the capture reagent.

After the binding has taken place, the amount of labeled conjugate bound to the capture reagent produces an optically-detectable intensity change at each detection zone 125, which can for example be optically read by an assay reader device to generate a signal having an intensity value corresponding to the saturation intensity of the detection zone 125. As described above, the saturation intensity read from a detection zone 125 is in an inverse relationship with the concentration of analyte present. Detection methods can include detecting, visually or via an optical reader device, a change in color, change in fluorescence, change in luminescence, change in other optical properties, or any other easily measured physical property indicating the presence or absence or quantity of the target antineoplastic molecule in the liquid sample.

The liquid sample 150 is carried further along the lateral flow path 145 to the control zone 130. The control zone 130 can comprise a region of the substrate 120 or a porous membrane coupled to the substrate 120, for example nitrocellulose. The control zone 130 can include non-diffusibly bound control reagents, for example arranged in a line ("control line"), that specifically bind to a control analyte provided in the test sample or the conjugate release zone. The control line is a form of quality control that ensures the liquid sample has migrated appropriately and its appearance can be used to validate the test result. An optically perceptible control line should still form for valid assays, regardless of the results on the test lines.

The liquid sample 150 then flows to an adsorbent or absorbent pad 135 at the opposing end of the test strip 100 from the sample receiving zone 110. This pad 135 can comprise cellulose fibers and is configured to wick the liquid sample 150 through the substrate 120 and to collect any liquid that flows to the end of the test strip 100. The pad 135 allows the use of larger sample volumes, which results in increased test sensitivity.

Overview of Example Testing Method

Figure 3A:
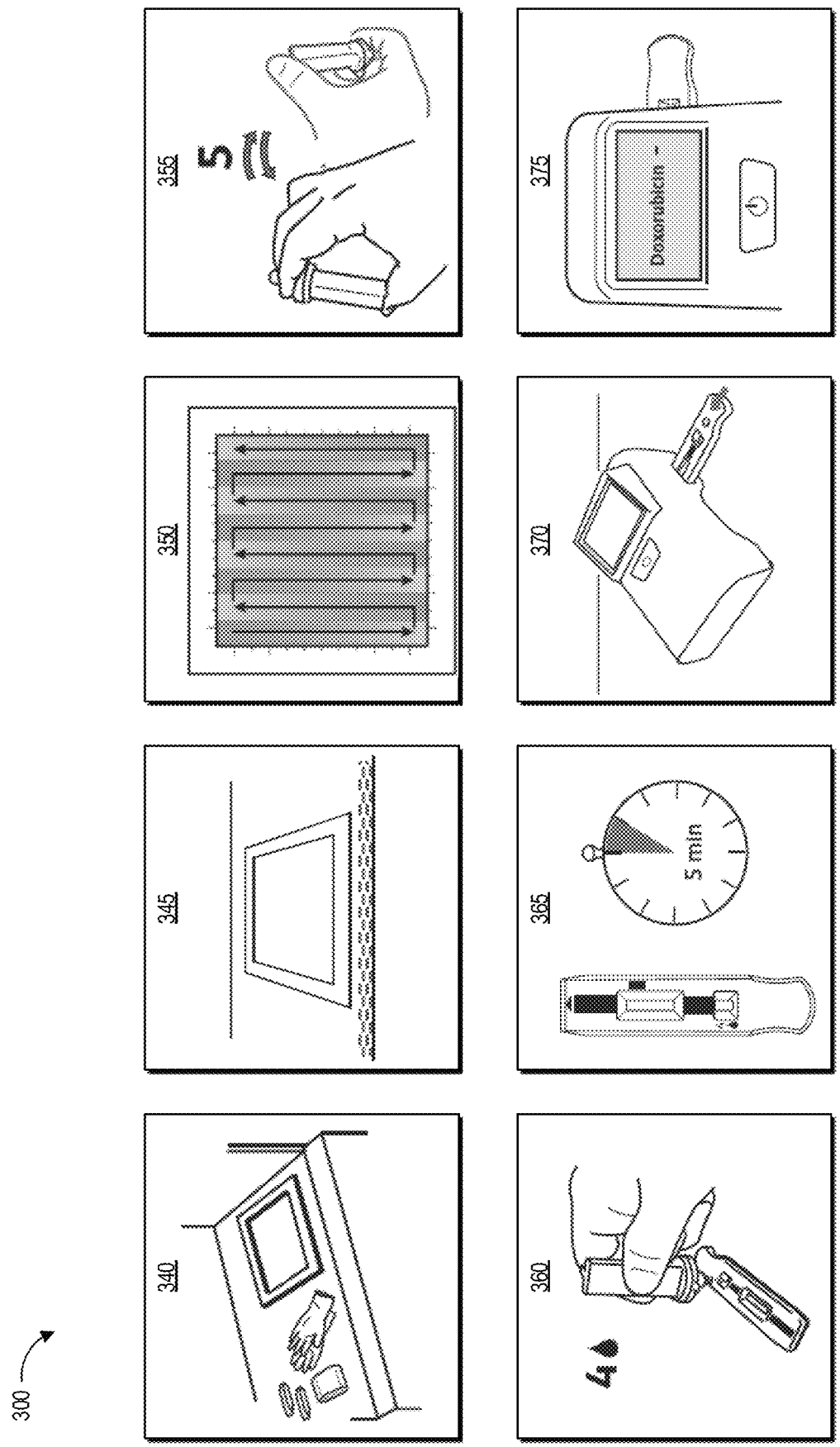
FIGS. 3A-3D graphically illustrate steps of an example method of collecting and testing a liquid sample as described herein.

FIGS. 3A-3D graphically illustrate steps of an example method of collecting and testing a liquid sample as described herein. FIG. 3A illustrates an example method 300 for obtaining a liquid sample from a test surface 250 potentially contaminated with hazardous drugs. One, some, or all of the depicted blocks of FIG. 3A can be printed as graphical user interface instructions on the packaging of an assay and/or collection kit, or can be presented on a display screen of an assay reader device, a test area terminal, or a personal computing device of the user.

At block 340, the user can identify a sample location and gather a collection kit, assay cartridges, and a template. The collection kit can include a swab attached to a handle and a collection container. In some examples, the swab is pre-wetted with buffer solution and packaged together with the handle in a first sealed pouch and the collection container is packaged in a second sealed pouch. The assay cartridge may include an assay device housed inside a cartridge having a window or port aligned with a sample receiving zone of the assay device. In one implementation, the assay device is a test strip, for example but not limited to a lateral flow assay test strip. Also at block 340 the user can put on clean gloves prior to each sample collection and/or opening of the collection kit, both to protect the user from potential contamination on the surface and to protect the collected sample from contamination on the user's hands.

At block 345, the user can establish a test area on the test surface. For example, the user can place a template (physical or augmented reality) over the intended location to clearly demarcate the area that will be swabbed. Also at block 345 the user can open the collection kit packaging, including opening the separately-packaged swab and handle.

At block 350, the user can swab the entire test area with the pre-moistened swab. The user can swab the test area using slow and firm strokes. As shown, the user can methodically pass the swab in straight lines along the height of the test area all the way across the width of the test area.

At block 355, the user can insert the swab into the collection container. In some examples, the collection container includes a t-shaped well. Though not illustrated, the swab may have a t-shaped cross-section that substantially matches that of the container well. The user seals the container with a top that includes a dripper cap, and fully inverts (e.g., turn upside down and then return to right-side-up) the sealed container five times. During these inversions, the liquid in the reservoir of the container washes primarily over the swab material due to the cross-sectional shape of the reservoir corresponding to the shape of the handle (as well as other features of the reservoir), and the handle slides within the reservoir due to the reservoir having a greater height than the handle. Thus, the inversion combined with the geometries of the container and handle and the flow of the buffer solution can extract collected contaminants from the swab material. In one non-limiting example, the user does not invert or agitate the container before moving to the next step.

At block 360, the user can leave the swab and handle inside the container, remove the dripper cap, and squeeze (or allow gravity to draw) one or more drops (for example but not limited to four drops) into the sample well on one or more assay cartridges. For example, in some embodiments the user may drop sample onto multiple assays each designed to test for a different drug. In some examples anywhere between three and ten drops can produce suitable results on the assay. A drop is an approximated unit of measure of volume corresponding to the amount of liquid dispensed as one drop from a dropper or drip chamber via gravitational pull (sometimes aided by a positive pressure created within the container holding the liquid). Though the precise volume of any given drop depends upon factors such as the surface tension of the liquid of the drop, the strength of the gravitational field pulling on the drop, and the device and technique used to produce the drop, it is commonly considered to be a volume of 0.05 mL. In alternate embodiments the user may mechanically couple a fluid transfer portion of the collection device to a fluid transfer portion of the assay device to release a controlled volume of sample through a closed fluid pathway, for example as shown in FIG. 4D.

At block 365, the user can use a timer to allow the sample to develop for a period of time. For example, the sample can develop for about one minute, about two minutes, about three minutes, about four minutes, about five minutes, about six minutes, or some other amount of time. Other development times are possible. In some embodiments the timer can be built in to the programming of the reader device that reads the assay. The development time can vary depending on the particular test that is being performed and the particular operating parameters of the assay device.

At block 370, the user can insert the assay cartridge into an assay reader device. The assay cartridge can be inserted into the ready device prior to or after the sample is developed, depending upon the operational mode of the device. In some embodiments, the user may sequentially insert multiple cartridges for testing different aspects of the sample or for ensuring repeatability of test results.

At block 375, the assay reader device reads portions of the inserted cartridge (including, for example, detecting optical signals from exposed areas of a capture zone of a test strip housed in the cartridge), analyzes the signals to determine optical changes to test zone location(s) and optionally control zone location(s), determines a result based on the optical changes, and displays the result to the user. The device can optionally store the result or transmit the result over a network to a centralized data repository. As illustrated, the device displays a negative result for the presence of Doxorubicin in the sample. In other embodiments the device can display a specific detected concentration level in the sample and/or determined for the test area, and optionally can display confidence values in the determined result.

After testing the user can re-seal the container with the dripper cap and dispose of the collection device and assay (for example in compliance with hazardous waste regulations). Optionally, the user can reconnect the reader device to its power supply, execute any needed decontamination procedures, re-test a decontaminated surface, and perform required reporting of the result.

Figure 3B:
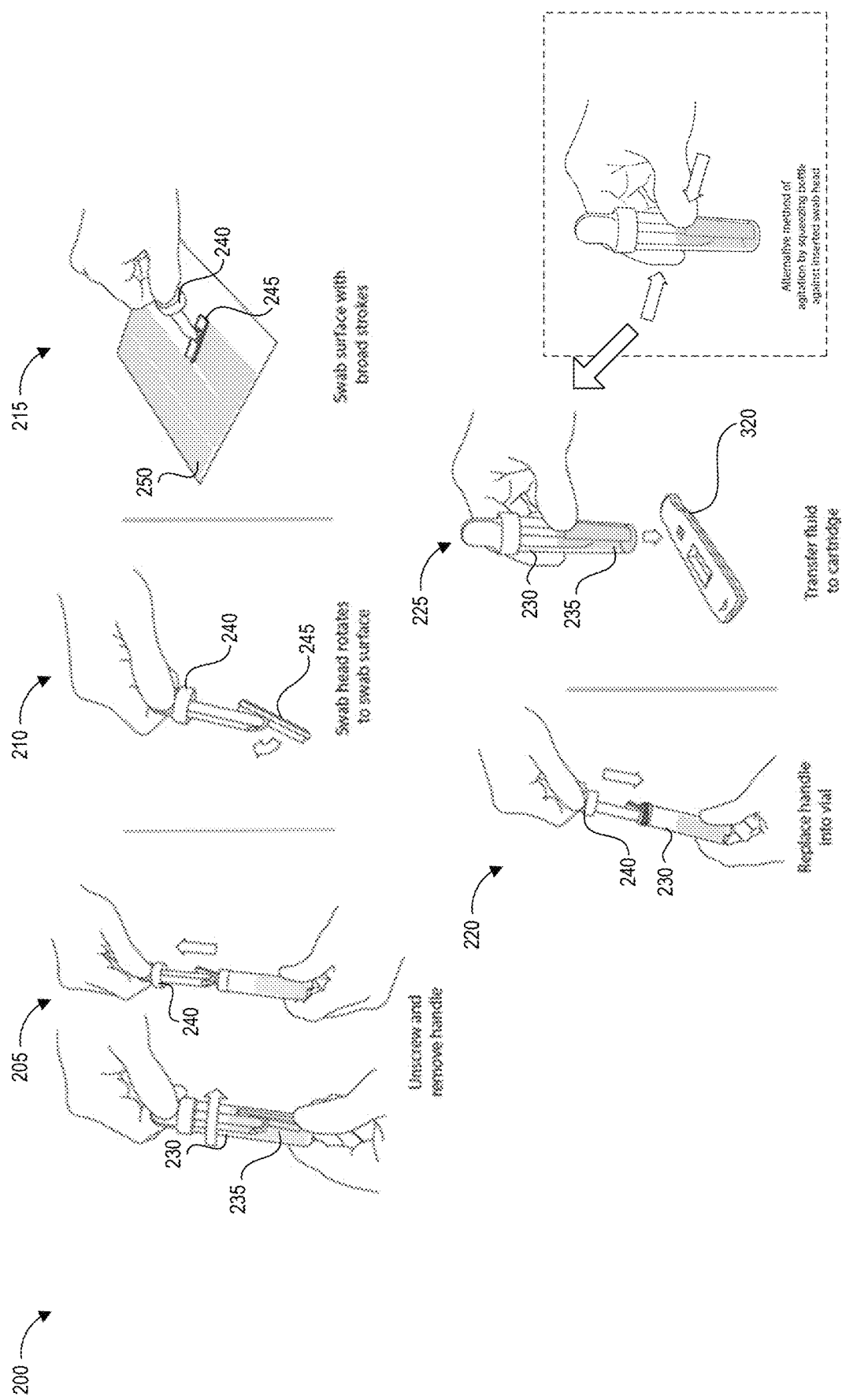

FIG. 3B illustrates another testing method 200 that depicts details of steps 350, 355, and 360 of the process 300 using an alternate embodiment of the collection device.

At step 205 a user can remove a handle 240 from a container 230 containing a predetermined volume of buffer fluid 235. The handle 240 has a swab 245 secured to one end that is pre-wetted with the buffer fluid 235. In other implementations the buffer fluid 235 can be provided separately, applied to the test surface, and absorbed using the swab 245. The buffer fluid 235 helps lift contaminants from the test surface into the swab and/or the user can separately apply fluid to the test surface.

At step 210, optionally in some embodiments the swab head can rotate to assist in maintaining contact between the swab 245 and the test surface 250.

At step 215, the user can swab a designated test area of the test surface 250. It can be preferable in some implementations to swab the entirety of the test area and only within the test area so as to generate an accurate measurement of the concentration of the contaminant, particularly for contaminants where small quantities per area are harmful to users. Swabbing the entirety of the test area and only within the test area can also allow a reader device as described herein to generate an accurate measurement of the concentration of the contaminant in situations where a very small amount of contaminant is present. Even if the amount of contaminant detected is very small and not immediately harmful to persons in the immediate area, detection of contaminant in any amount can alert the user to a leak or unintended release of hazardous material. Further, for some hazardous drugs there is no safe exposure level. As such, some embodiments of the process 200 can include placing a guide or template over the test area to assist the user with swabbing only a predetermined area.

At step 220, the user can replace the swab and handle into the collection container 230. Optionally, the user and/or structure of the container can agitate the swab to release collected contaminants into the fluid within container. For example, step 255 shows the option of the user squeezing the sides of the container against the swab head.

At step 225, the user can transfer fluid to a cartridge 320 containing a test strip, for example test strip 100 described above or test strips 400A, 400B described below, or to another test device. For example, the user can drip fluid from the container 230 onto the sample receiving zone. In some embodiments, the cartridge 320 and container 230 can be structured to mechanically mate via fluid-tight connection so as to prevent accidental exposure of users or the testing environment to potentially contaminated fluid.

Lateral flow assay test systems described herein can include a lateral flow assay test device (such as but not limited to a test strip, such as assay test strip 100), a housing including a port configured to receive all or a portion of the test device, a reader including a light source and a light detector, a data analyzer, and combinations thereof. A housing may be made of any one of a wide variety of materials, including plastic, metal, or composite materials. The housing forms a protective enclosure for components of the diagnostic test system. The housing can also define a receptacle that mechanically registers the test strip with respect to the reader. The receptacle may be designed to receive any one of a wide variety of different types of test strips. In some embodiments, the housing is a portable device that allows for the ability to perform a lateral flow assay in a variety of environments, including on the bench, in the field, in the home, or in a facility for domestic, commercial, or environmental applications.

A reader may include one or more optoelectronic components for optically inspecting the exposed areas of the capture zone of the test strip. In some implementations, the reader includes at least one light source and at least one light detector. In some embodiments, the light source may include a semiconductor light-emitting diode and the light detector may include a semiconductor photodiode. Depending on the nature of the label that is used by the test strip, the light source may be designed to emit light within a particular wavelength range or light with a particular polarization. For example, if the label is a fluorescent label, such as a quantum dot, the light source would be designed to illuminate the exposed areas of the capture zone of the test strip with light in a wavelength range that induces fluorescent emission from the label. Similarly, the light detector may be designed to selectively capture light from the exposed areas of the capture zone. For example, if the label is a fluorescent label, the light detector would be designed to selectively capture light within the wavelength range of the fluorescent light emitted by the label or with light of a particular polarization. On the other hand, if the label is a reflective-type label, the light detector would be designed to selectively capture light within the wavelength range of the light emitted by the light source. To these ends, the light detector may include one or more optical filters that define the wavelength ranges or polarizations axes of the captured light. A signal from a label can be analyzed, using visual observation or a spectrophotometer to detect color from a chromogenic substrate; a radiation counter to detect radiation, such as a gamma counter for detection of $^{125}$I; or a fluorometer to detect fluorescence in the presence of light of a certain wavelength. Where an enzyme-linked assay is used, quantitative analysis of the amount of an analyte of interest can be performed using a spectrophotometer.

In some embodiments, the label used by the test strip may be magnetic nanoparticle labels configured to generate magnetic signals. As such, the reader can be modified to detect the strengths of these magnetic signals rather than optically-detectable changes. Thus, in the present disclosure, description of a reader detecting optically-detectable changes can apply to alternate embodiments that instead detect magnetically-detectable changes. In addition, it will be understood that "signal" may refer to an optical signal, a fluorescence signal, a magnetic signal, or any other type of signal occurring due to the test strip labels.

Figure 3C:
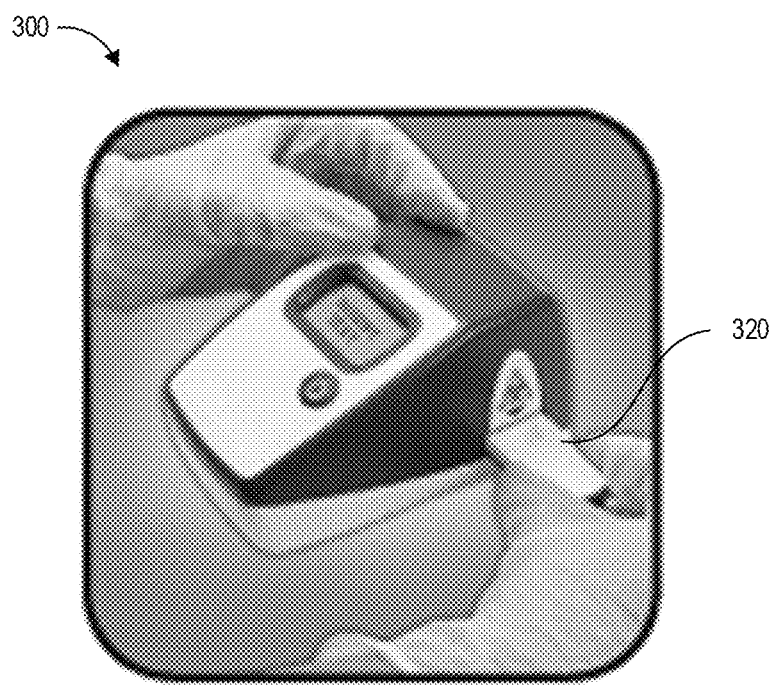
Figure 3D:
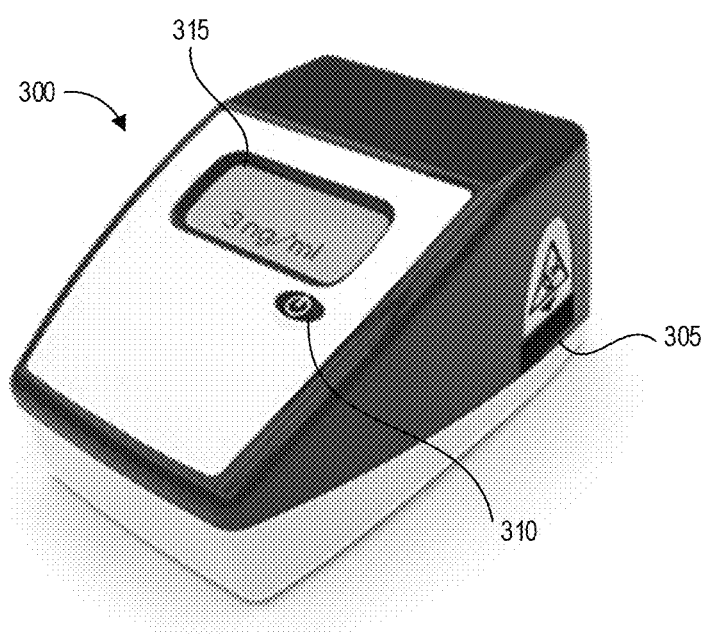

FIG. 3C illustrates a further step of inserting the cartridge 320 into an aperture 305 of reader device 300. Although the following example is described with reference to reader device 300, an assay test device (whether housed within cartridge 320 or not housed within a cartridge) can be read by any suitable reader as described above. Further, though not illustrated, further steps can include operating the reader device 300 to perform detection and analysis of the test strip and displaying results of the test. FIG. 3D illustrates the reader device 300 displaying a test result on display 315. In this case, the test result indicates a concentration of the analyte of interest of 3 ng/ml.

The device 300 can be an assay reader device having an aperture 305 for receiving an assay test strip and cartridge 320 and positioning the test strip so that the detection zones are positioned in the optical path of detection components located inside the device 300. In some cases, the detection components can include imaging components that image portions of the assay test strip and cartridge 320 to detect optical changes in the assay test strip. The device can also use these or additional imaging components to scan a bar code on the cartridge, for example to identify which detection techniques and analysis to perform.

Some embodiments of the device 300 can be configured to perform an initial scan, for example using a bar code scanner to scan one or more bar codes. A bar code can identify the type of test to be performed, the person conducting the test, the location of the test, and/or the location in the facility of the test surface (for example pharmacy, nursing area, cabinet #, bed #, chair #, pump #, etc.) After reading any bar code identifiers the cartridge 320 is then inserted into the reader as shown in FIGS. 3A and 3C. Barcodes are provided as an illustrative example, and in various embodiments other identification patterns can be provided for reading by the device 300, for example serial numbers, graphical identifiers, radio frequency ID transmitters, and the like.

The device 300 can have a button 310 that readies the device for use and provides an input mechanism for a user to operate the device. In some embodiments device operation mode can be set via a number or pattern of clicks of the single button 310 of the device 300. For example, in some implementations a single press of the button 310 can power on the device 300 and set the device 300 to a default operation mode, and the device 300 can implement the default operation mode upon insertion of a cartridge. A double click of the button 310 can initiate an alternate operation mode that is different than the default operation mode. Other numbers or patterns of pressing the single button 310 by a user can provide instructions to the processor of the device regarding a desired operation mode. Embodiments of a device 300 are described herein with reference to a single button, but other features allowing a user to select and switch between device operation modes are possible (such as but not limited to a single switch, knob, lever, or handle).

One example of a device operation mode is end-point read mode. In the end-point read mode, the user prepares and incubates the assay outside of the device 700 and tracks the development time of the assay. For example, an assay for determining Methotrexate or Doxorubicin concentration can have a development time of 5 minutes, so the user would apply the fluid to the assay from a collection device as described herein and wait for 5 minutes. At the end of the 5 minutes the user would insert the assay 320 into the device 300 to obtain a test result. Accordingly, when operating in end-point read mode the device 300 can provide instructions, for example audibly or on a visual display, that instruct a user to wait for a predetermined time after applying a sample to an assay before inserting the assay in the device 300. In other embodiments, when operating in end-point read mode the device 300 may not display any instructions but may simply read an assay upon insertion into the device 300. Upon insertion of the assay into the base device 300, an optical reader of the device can collect data (for example, image data) representing the assay for analysis in determining a result of the assay. In some embodiments end-point read mode can be the default operation mode of the device 300.

Another example of a device operation mode is walkaway mode. When operating in walkaway mode, the device 300 can provide instructions for the user to insert the assay immediately after application of the sample. In the walkaway mode according to one embodiment, the user can apply the specimen to the assay and immediately insert the assay into the device 300. The assay will develop inside the device 300 and the device 300 can keep track of the time elapsed since insertion of the assay 320. At the end of the predetermined development time, the device 300 can collect data representing optical changes in the assay, analyze the data to determine a test result, and report the test result to the user. The assay development time can be unique to each test. In some embodiments walkaway mode can be set by double-clicking the single button 310 of the device 300. Further input can indicate the assay development time to the reader device. For example, a barcode scanned by a barcode reader, or a barcode provided on the assay or on a cartridge used to hold the assay, can indicate to the device 300 a type of assay that is inserted and a development time for that assay. Based upon the type of assay, the device 300 can wait for the predetermined amount of time after sample application and insertion before collecting data representing optical changes in the assay.

There are many advantages associated with the ability of a user to select and switch between device operation modes in implementations of assay analyzers described herein. The endpoint read mode can be convenient in large laboratories or medical practice facilities where personnel typically batch process a number of tests. The walkaway mode can be useful when a single test is being performed, or when the end user does not want to have to track the assay development time (or is not knowledgeable or not trained on how to track the assay development time accurately). The walkaway mode can advantageously reduce or eliminate the occurrence of incorrect test results due to an assay being inserted and read (for example, imaged) too quickly (too soon before the development time of the assay has elapsed) or too slowly (too long after the development time of the assay has elapsed). Further, in walkaway mode the assay reader can operate to inspect the assay (for example, capture multiple images of the assay) at predetermined time intervals, for example when a kinetic graph of the assay readings is desired.

One embodiment of the disclosed device 300 includes only a single button 310 on its exterior housing, such as a single power button that powers the device 300 off and on. Embodiments of the disclosed device 300 also implement two different device operation modes (although more than two device operation modes are possible). In order to enable the end user to select and switch between the two device operation modes, the device 300 can include instructions to implement a double-click function on the power button. After receiving input of a single press of the button to power on the device, insertion of an assay cartridge can automatically trigger end-point read mode. When the processor of the device receives input from a user double-clicking the power button, this can initiate the stored instructions to implement the walkaway mode. This double-click functionality offers a simple and intuitive way for the end user to switch between different operation modes of the base assay analyzer. The double-click functionality also enables the user to configure the device in real time to operate in the walkaway mode without requiring any additional configuration steps or additional programming of the device 300 by the user. It will be appreciated that the device 300 can be provided with instructions to recognize other click modes instead of or in addition to the double-click to trigger secondary (non-default) device operation modes, for example to recognize a user pressing the button any predetermined number of times, pressing the button in a predetermined pattern, and/or pressing and holding the button for a predetermined length of time.

The device 300 can also include a display 315 for displaying instructions and/or test results to the user. After insertion of the test strip, the device 300 can read a bar code on the assay test strip to identify the name and/or concentration range of the drug. The device 300 can inspect the inserted test strip (in one example, by "imaging" the strip or otherwise emitting light towards the test strip and then detecting the intensity of a signal representing detected light reflected from the test strip), and analyze the signals representing the inspected test strip to calculate results, display the results to the user, and optionally transmit and/or locally store the results. The results can be calculated and displayed as contamination with an indication of positive or negative (for example, +/−; yes/no; etc.), and/or an actual contamination (analyte of interest) per area (for example, Drug Concentration=0.1 ng/cm$^2$), and/or an actual amount of contamination (analyte of interest) per volume (for example, Drug Concentration=3 ng/ml). These indications are non-limiting examples as other indications and measurement units are also suitable.

Some embodiments of the device 300 may simply display the result(s) to the user. Some embodiments of the device 300 may also store the result(s) in an internal memory that can be recalled, for example, by USB connection, network connection (wired or wireless), cell phone connection, near field communication, Bluetooth connection, and the like. The result(s) can also automatically be logged into the facility records and tracking system. The device 300 can also be programmed to automatically alert any additional personnel as required, without further input or instruction by the user. For example, if the device 300 reads contamination levels that are above the threshold of human uptake and considered hazardous to for human contact, a head pharmacist, nurse, manager, or safety officer can be automatically notified with the results and concentration of contamination to facilitate a rapid response. The notification can include location information, such as but not limited to a geographic position (latitude/longitude) or description of location (Hospital A, Patient Room B, etc.). That response may include a detailed decontamination routine by trained personnel or using a decontamination kit provided together or separately from the hazardous contamination detection kit.

In some embodiments, device 300 can be a special-purpose assay reader device configured with computer-executable instructions for identifying trace concentrations of contaminants in the samples applied to test strips. Further components of the device 300 are discussed below with respect to the diagram of FIG. 5.

Overview of Example Tuned Assays and Reader Devices

Figure 4A:
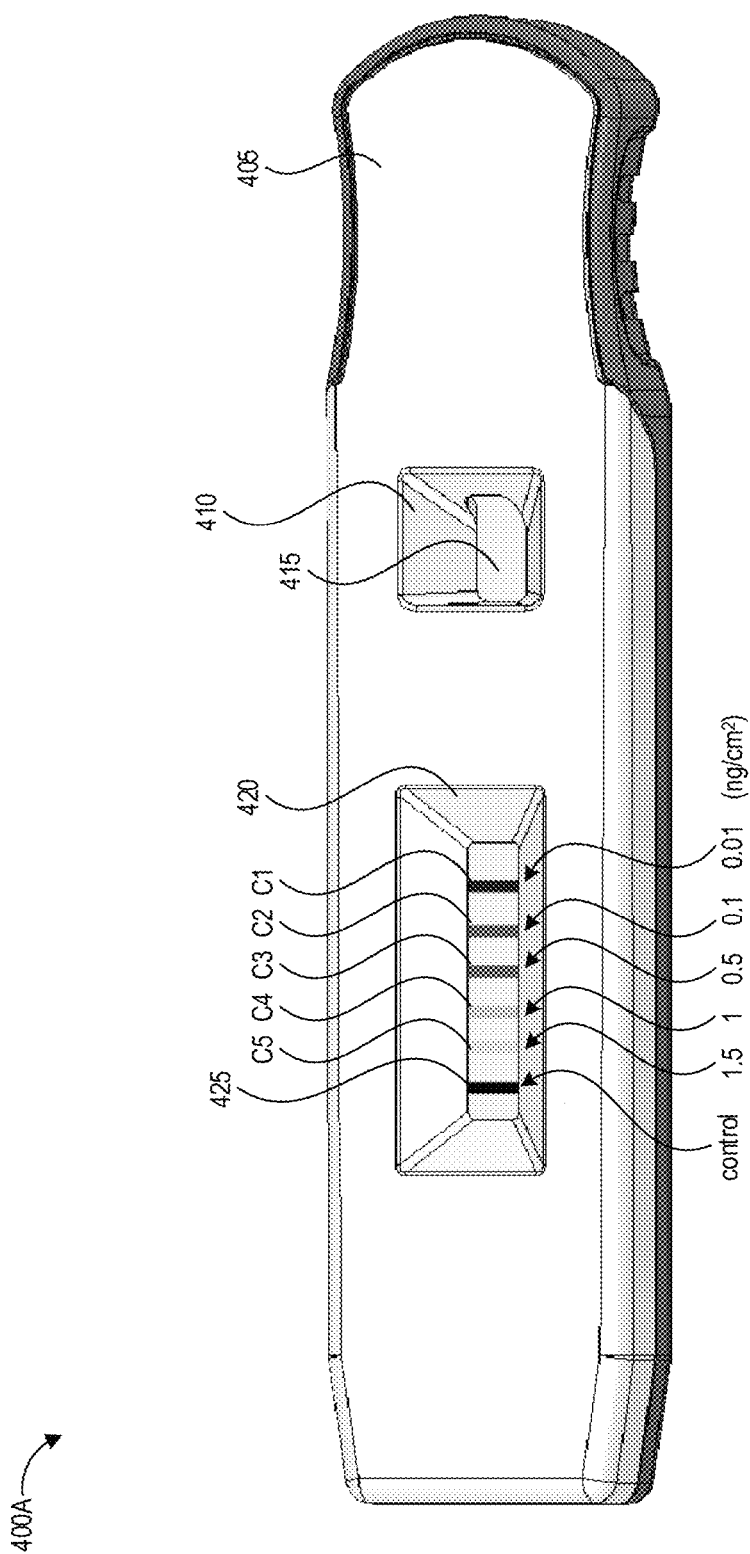
FIG. 4A depicts an example test strip having a number of detection zones each tuned to a different concentration level.
Figure 4B:
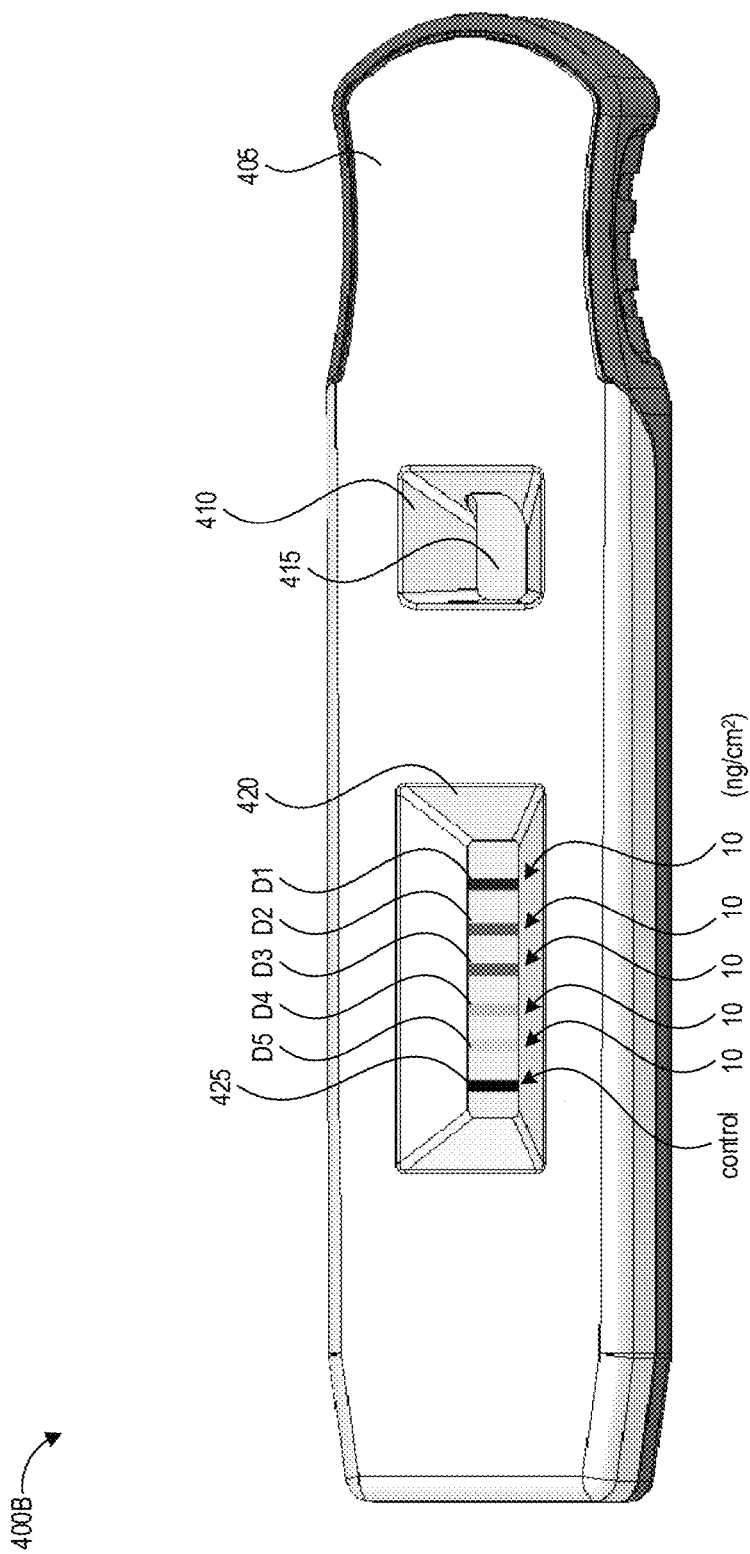
FIG. 4B depicts an example test strip having a number of detection zones that can each be read, wherein the read saturation levels can be used together to generate a total concentration reading.
Figure 4C:
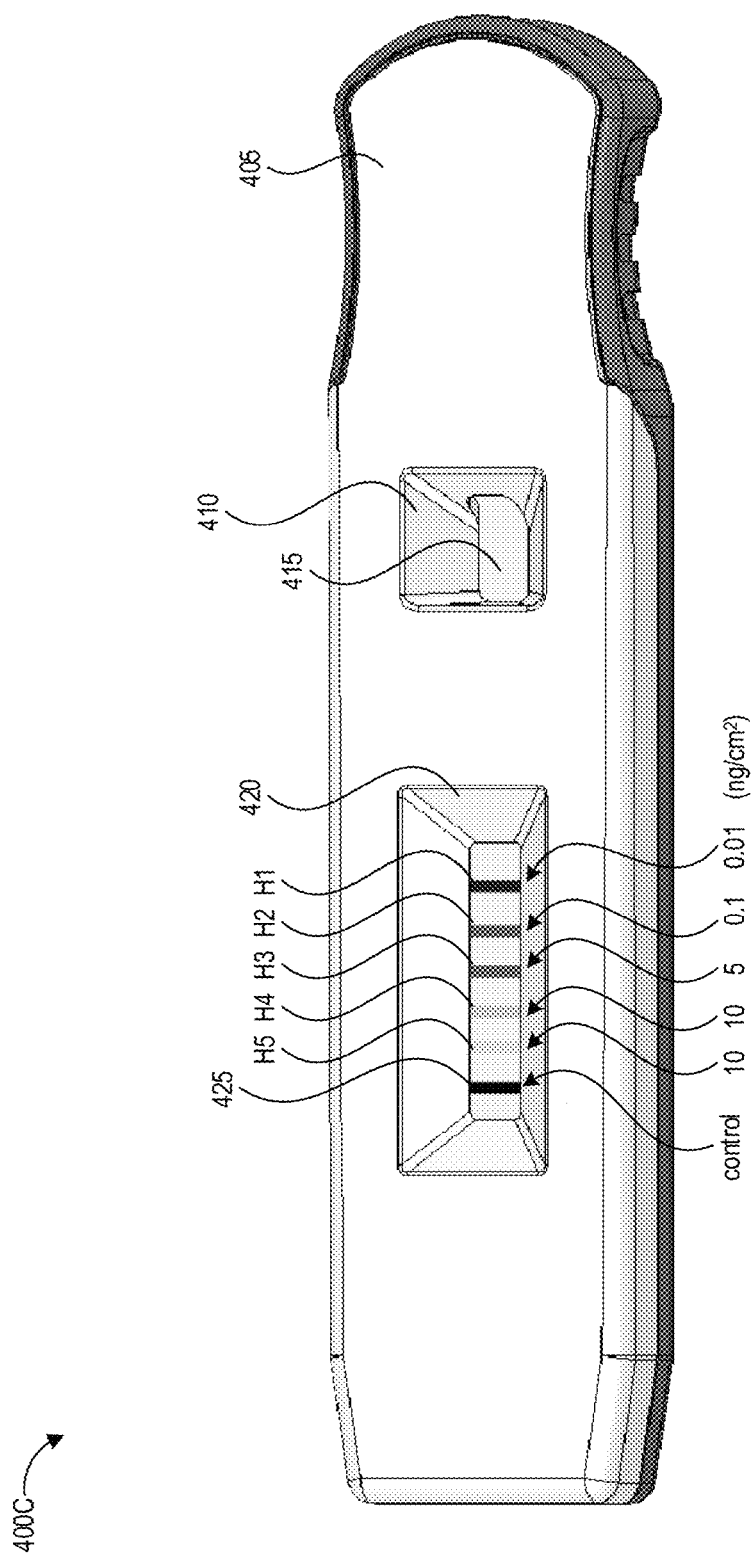
FIG. 4C depicts an example test strip including a hybrid detection model drawing from the models described with respect to both FIGS. 4A and 4B.
Figure 4D:
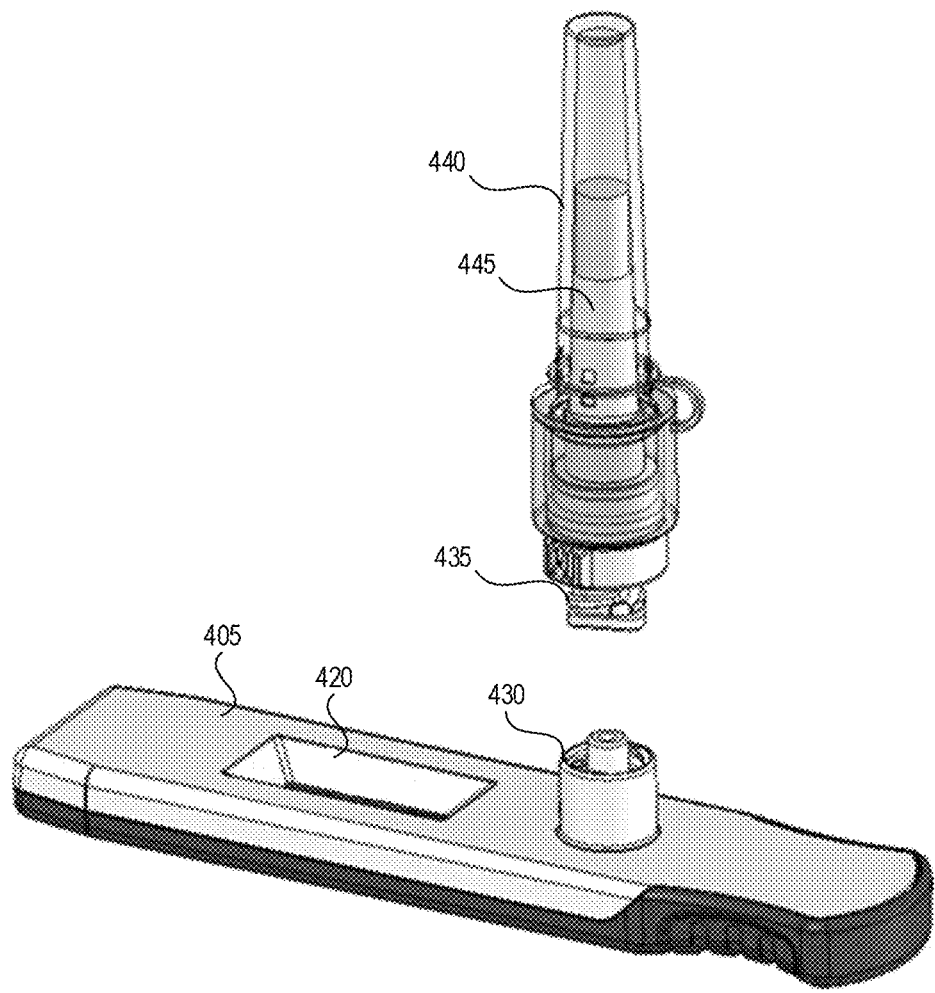
FIGS. 4D and 4E illustrate various embodiments of a cartridge that can be used to house a test strip as described herein.

FIG. 4A depicts an example test strip 400A having a number of detection zones C1-C5 each tuned to a different concentration level. FIG. 4B depicts another embodiment of the test strip 400B having a number of detection zones D1-D5 that can each be read to determine saturation level, with these readings combined to determine total concentration in the sample. FIG. 4C depicts an example test strip including a hybrid detection model drawing from the multiple concentration levels model described with respect to FIG. 4A and the multiple saturation levels model described with respect to model described with respect to 4B.

With reference to FIGS. 4A-4C, the test strips 400A, 400B, 400C can be the test strip 100 in some embodiments, and are each depicted within a cartridge 405 having a first window 410 exposing a sample receiving zone 415 of the test strip 400A and a second window 420 exposing the detection zones C1-C5 and a control zone 425. The sample receiving zone 415 can be the sample receiving zone 110 in some embodiments, and can receive the liquid sample and prepare it for interaction with remaining zones of the test strip 400A, 400B, 400C. A conjugate release zone (not pictured, see zone 115 of FIG. 2 for reference) can be positioned in the lateral flow path between the sample receiving zone 415 and the detection zones in order to release labeled conjugate into the liquid sample. The sample can then flow through the detection zones and interact with immobilized capture reagent before flowing through control zone 425. A line should form in control zone 425 to validate the assay regardless of the outcome of the detection zones.

When used with the control zone 425, the test strip 400A, 400B, 400C may indicate that enough signal was detected (with statistical factors considered relating to sample collection efficiency, sampling error, measurement error, false positive, false negative, and any other factors deemed influential on the accuracy of test results). For example, with reference to the example of FIG. 4A, the test strip 400A can indicate that enough confidence was met to deem that the sample concentration passed the 0.01, 0.1, and 0.5 thresholds. If not enough confidence was shown in the 1.0 and 1.5 concentration lines, the end user may be notified (e.g., by a reader device) that their test yielded a certain confidence that their sample was at least greater than 0.5 ng/cm$^2$. The benefit of lower sets of resolution may be useful for tracking and analysis. Facilities can determine whether people or procedures are effective by watching the thresholds increase or decrease over the course of many test procedures.

Example Assays that Increase Dynamic Range of a Single Test Strip Using Threshold Levels With reference to FIG. 4A, each of the five detection zones C1-C5 can comprise immobilized capture reagents as described above, with each detection zone tuned to a different level of concentration of the same target antineoplastic drug in the liquid sample. Such tuning can account for the interactions between target antineoplastic molecules and/or labeled conjugate with other detection zones (e.g. detection zones positioned earlier in the lateral flow path). In some embodiments, the detection zones can be arranged along the lateral flow path in increasing order based on their tuned concentrations.

To illustrate, consider the following example concentrations for detection zones C1-C5. The first detection zone C1 can be tuned to fully saturate at a concentration of 0.01 ng/cm$^2$ of the target antineoplastic molecule in the liquid sample flowing through detection zone C1 from the sample receiving zone 415. The second detection zone C2 can be tuned to fully saturate at a concentration of 0.1 ng/cm$^2$ of the target antineoplastic molecule in the liquid sample. This sensitivity can be tuned to account for the fact that the liquid sample flowing through the second detection zone C2 has already flowed through and interacted with the capture reagent in the first detection zone C1. The third detection zone C3 can be tuned to fully saturate at a concentration of 0.5 ng/cm$^2$ of the target antineoplastic molecule in the liquid sample. Again, this sensitivity can be tuned to account for the fact that the liquid sample flowing through the third detection zone C3 has already flowed through and interacted with the capture reagent in the first and second detection zones C1, C2. The fourth detection zone C4 can be tuned to fully saturate at a concentration of 1.0 ng/cm$^2$ of the target antineoplastic molecule in the liquid sample. Again, this sensitivity can be tuned to account for the fact that the liquid sample flowing through the fourth detection zone C4 has already flowed through and interacted with the capture reagent in the first, second, and third detection zones C1-C3. The fifth detection zone C5 can be tuned to fully saturate at a concentration of 1.5 ng/cm$^2$ of the target antineoplastic molecule in the liquid sample. Again, this sensitivity can be tuned to account for the fact that the liquid sample flowing through the fifth detection zone C5 has already flowed through and interacted with the capture reagent in the first, second, third, and fourth detection zones C1-C4.

It will be appreciated that greater or fewer detection zones can be implemented according to this principle in other implementations, and that the tuned concentrations can vary from this illustrative example.

An assay reader device, for example device 300 described above or device 500 described below, can be programmed with executable instructions to read these detection zones C1-C5 and determine a concentration of the target antineoplastic molecule in the liquid sample based on the signals read from some or all of the detection zones C1-C5. As described herein, the reader device can have an optical reading device positioned to receive light reflected from the detection zones C1-C5 and to generate a plurality of signals each having an intensity corresponding to the saturation level of a corresponding detection zone. The reader device can access information representing number and locations of the test lines and the concentration level to which each test line is tuned, for example by reading a machine-readable feature or pattern on the cartridge 405. The machine-readable feature can be optically-detectable, for example a barcode, serial number, or other graphical pattern, and the reader can include a suitable optical or electronic scanning mechanism (e.g., a barcode reader or imager). In other embodiments the machine-readable feature can be read by the reader device by any other suitable electronic scanning mechanism, including but not limited to RFID scanning mechanisms, magnetic signal detecting mechanisms, and OCR scanning mechanisms.

In some implementations, the signal read from each detection zone can be compared to a threshold to determine whether that detection zone was sufficiently saturated. For example, the reader device can be programmed to identify a detection zone as sufficiently saturated if the signal intensity indicates that the saturation of the test line was greater than or equal to a threshold percentage of full saturation (e.g., 50%, 75%, 90%, 95%, 100%, etc.). The reader device can identify the antineoplastic drug concentration using the concentration level of the sufficiently saturated detection zone located farthest along the lateral flow path, that is, farthest from the sample receiving zone 415.

Continuing with the example provided above, consider that the reader device determined that the saturation levels of detection zones C1, C2, and C3 were greater than or equal to the saturation threshold. Of these, detection zone C3 is farthest along the lateral flow path. Accordingly, the reader device can output that the drug concentration is equal to 0.5 ng/cm$^2$, the concentration level to which detection zone C3 is tuned.

In some implementations, the reader device can additionally indicate a confidence in the reading. This can be based, for example, on the saturation levels of the sufficiently saturated detection zones (e.g., a mean of the saturation levels) or the saturation level of the sufficiently saturated detection zone located farthest along the lateral flow path. Returning to the example above, if detection zone C3 was 96% saturated, one implementation can output a 96% confidence level in the determined concentration.

Some implementations can further indicate that, although other detection zones did not meet the threshold, that there is a certain level of confidence that the sample contains a higher concentration. For example, if detection zone C4 was 69% saturated, one implementation can output a 69% confidence level that the determined concentration may be 1.0 ng/cm$^2$. Some implementations can combine the saturation levels and concentrations of any remaining detection zones to generate this additional information. Another implementation can output a general indication that the test yielded a certain level of confidence that the concentration was at least greater than 0.5 ng/cm$^2$, the concentration level determined based on detection zone C3.

Example Assay that Increases Dynamic Range of a Single Test Strip by Summing Results of Multiple Detection Zone Locations With reference to FIG. 4B, in one implementation detection zones D1-D5 can each be tuned to the same concentration, and the total concentration can be based on this concentration as well as saturation levels of each zone. In some embodiments the concentrations to which detection zones D1-D5 are tuned can differ from one another. Such tuning can account for the interactions between target antineoplastic molecules and/or labeled conjugate with other detection zones (e.g. detection zones positioned earlier in the lateral flow path).

To illustrate, consider the following example. Each of detection zones D1-D5 can be tuned to detect 10 ng/cm$^2$ of the target antineoplastic molecule in the liquid sample. The first detection zone D1 can be tuned to fully saturate at 10 ng/cm$^2$ of the target antineoplastic molecule in the liquid sample flowing through detection zone D1 from the sample receiving zone 415. The second detection zone D2 can be tuned to fully saturate at 10 ng/cm$^2$ of the target antineoplastic molecule in the liquid sample, with this sensitivity tuned for the fact that the liquid sample flowing through the second detection zone D2 has already flowed through and interacted with the capture reagent in the first detection zone D1. The third detection zone D3 can be tuned to fully saturate at 10 ng/cm$^2$ of the target antineoplastic molecule in the liquid sample, with this sensitivity tuned to account for the fact that the liquid sample flowing through the third detection zone D3 has already flowed through and interacted with the capture reagent in the first and second detection zones D1, D2. The fourth detection zone D4 can be tuned to fully saturate at 10 ng/cm$^2$ of the target antineoplastic molecule in the liquid sample, with this sensitivity tuned to account for the fact that the liquid sample flowing through the fourth detection zone D4 has already flowed through and interacted with the capture reagent in the first, second, and third detection zones D1-D3. The fifth detection zone D5 can be tuned to fully saturate at 10 ng/cm$^2$ of the target antineoplastic molecule in the liquid sample, with this sensitivity tuned to account for the fact that the liquid sample flowing through the fifth detection zone D5 has already flowed through and interacted with the capture reagent in the first, second, third, and fourth detection zones D1-D4.

It will be appreciated that greater or fewer detection zones can be implemented according to this principle in other implementations, and that the tuned concentrations can vary from this illustrative example. For example, in another implementation the tuned concentrations of detection zones D1-D5 can vary from one another, as described above with respect to detection zones C1-C5.

The assay reader device (e.g., devices 300, 500 described herein) can be programmed with executable instructions to read these detection zones D1-D5 and determine a concentration of the target antineoplastic molecule in the liquid sample based on a combination of the signals read from the detection zones D1-D5. The reader device can access information representing number and locations of the test lines and the concentration level to which each test line is tuned, for example by reading a barcode on the cartridge 405.

Considering the example above, the reader device can generate signals indicating that detection zone D1 is 95% saturated, detection zone D2 is 85% saturated, detection zone D3 is 70% saturated, detection zone D4 is 40% saturated, and detection zone D5 is 10% saturated. The reader device can be programmed with instructions to multiply each saturation level by the concentration level to which the corresponding detection zone has been tuned to obtain a concentration product value, and then to sum the obtained concentration product values to identify a total concentration of analyte of interest (for example but not limited to a total concentration of antineoplastic drug) in the sample. In this example, the reader would calculate that the sample applied to the test strip has a concentration of [(10*0.95)+(10*0.85)+(10*0.70)+(10*0.40)+(10*0.10)], or 30 ng/cm$^2$.

Example Assay that Increases Dynamic Range of a Single Test Strip by Dedicating Some Detection Zones to Provide Threshold Level Information but Also Summing Results of all Detection Zone Locations to Provide Total Concentration Information With reference to FIG. 4C, in one implementation detection zones H1-H5 can each be tuned to a mix of thresholds and concentrations, and the total concentration can be based on these concentrations as well as saturation levels of each zone.

Each of detection zones H1-H5 can be tuned to fully saturate at a certain concentration of the target antineoplastic molecule in the liquid sample, and can be used by a reader device for a hybrid approach that seeks to identify both whether the concentration of the target antineoplastic molecule in the liquid sample passes one or more thresholds and to identify a total concentration using summation as described with respect to FIG. 4B. For example, some lower threshold levels can be detected (or any threshold levels desired) and then some or all of the detection zones can be summed for a composite result.

To illustrate, consider the following example. The first detection zone H1 can be tuned to fully saturate at a concentration of 0.01 ng/cm$^2$ of the target antineoplastic molecule in the liquid sample flowing through detection zone H1 from the sample receiving zone 415. The second detection zone H2 can be tuned to fully saturate at a concentration of 0.1 ng/cm$^2$ of the target antineoplastic molecule in the liquid sample. This sensitivity can be tuned to account for the fact that the liquid sample flowing through the second detection zone H2 has already flowed through and interacted with the capture reagent in the first detection zone H1. In this example, the detection zones H1 and H2 operate similarly to detection zones C1 and C2 described above.

The third detection zone H3 can be tuned to fully saturate at a concentration of 5.0 ng/cm$^2$ of the target antineoplastic molecule in the liquid sample. Again, this sensitivity can be tuned to account for the fact that the liquid sample flowing through the third detection zone H3 has already flowed through and interacted with the capture reagent in the first and second detection zones H1, H2. The fourth detection zone H4 can be tuned to fully saturate at 10 ng/cm$^2$ of the target antineoplastic molecule in the liquid sample, with this sensitivity tuned to account for the fact that the liquid sample flowing through the fourth detection zone H4 has already flowed through and interacted with the capture reagent in the first, second, and third detection zones H1-H3. The fifth detection zone H5 can be tuned to fully saturate at 10 ng/cm$^2$ of the target antineoplastic molecule in the liquid sample, with this sensitivity tuned to account for the fact that the liquid sample flowing through the fifth detection zone H5 has already flowed through and interacted with the capture reagent in the first, second, third, and fourth detection zones H1-H4. Here, the detection zones H3-H5 operate similarly to detection zones D3-D5 described above, with the difference that detection zone H3 is configured to fully saturate at a different concentration level than detection zones H4 and H5.

A hybrid of the reading techniques to that described above with respect to FIGS. 4A and 4B can be applied to the test strip of FIG. 4C. In such a hybrid configuration, the reader device can still base the total concentration on the signals read from less saturated detection zones, because the readings of all zones are combined. Using the non-limiting example concentration levels described above for detection zones H1-H5, the readout method described with respect to FIG. 4C can calculate a total concentration of analyte of interest is [(0.01*0.95)+(0.1*0.90)+(5*0.60)+(10*0.30)+(10*0.15)], or 7.6 ng/cm$^2$. Further, the reader can determine based on the saturation levels of the "threshold" detection zones H1 and H2 that enough confidence was (or was not) met to deem that the sample concentration passed the 0.01 and 0.1 thresholds. Thus, the reader may output a test result indicating that the test at least met the threshold for 0.1 ng/cm$^2$, but that the total concentration is nearer to 7.6 ng/cm$^2$, possibly outputting that the total concentration was determined with less confidence.

It will be understood that other concentration levels are possible, depending on the particular analyte of interest and required or optimal test sensitivity requirements. Some implementations of the reader device can display, as just one example, an indication to users that there is a high confidence that the tested sample has at least met the threshold for 0.1 ng/cm$^2$ but it is likely that the total concentration is nearer to or close to 7.6 ng/cm$^2$. The reader device may provide a confidence value for the total concentration, for example based on the various saturation levels of some or all of the detection zones.

Further, the computations performed by the reader can vary across the detection zones H1-H5. For example, if the reader determines that not enough confidence was met to determine that the concentration of antineoplastic drug in the sample passed the H1 threshold, the reader may disregard any signals detected from the H2-H5 zones in its computations for determining the test result. As another example, if the reader determines that enough confidence was met to determine that the sample concentration passed the H1 and H2 thresholds, then the reader can sum the products of the concentration tunings of detection zones H3-H5 multiplied by the read signal intensities of these detection zones to compute the sample concentration. It will be appreciated that the specific designations of H1-H5 as either threshold or summation detection zones can vary across embodiments, and that greater or fewer detection zones can be used in various embodiments.

As such, using the hybrid model represented by FIG. 4C, each detection zone H1-H5, standing on its own, may provide valuable threshold level information to the user. For example, consider the scenario where only the H1 zone changes optically—the reader device can still obtain a threshold value from the test strip 400C. In addition, each individual detection zone H1-H5 can provide valuable information in an additional way. Optical changes in one zone can contribute to obtaining a total concentration reading for the entire test strip, where that total concentration reading has a higher dynamic range than if the test strip only included one detection zone. Thus, this embodiment combines the benefits of both the FIG. 4A and FIG. 4B embodiments.

Overview of Example Assay Systems

FIG. 4D illustrates another embodiment of the cartridge 405 that can be used to house any of the test strips 400A, 400B, 400C. Instead of the open well 410 exposing the sample receiving zone 415, the cartridge embodiment of FIG. 4D has a fluidic connector 430 configured to mechanically mate with a corresponding fluidic connector 435 of a sample collection container 440. Collection container can be used to collect a liquid sample 445 from a test surface as described above with respect to FIGS. 3A and 3B. Beneficially, the user can couple the fluidic connectors 430, 435 to create a liquid-tight seal between the cartridge 405 and the collection container 440 for transfer of the collected sample 445 to the test strip. This can prevent any leakage of the sample, which potentially contains hazardous contaminants. Such leakage could present health risks to the user, as well as to others exposed to an environment contaminated by such leaks. One suitable example of the connector 430 is a Leur Lock.

Figure 4E:
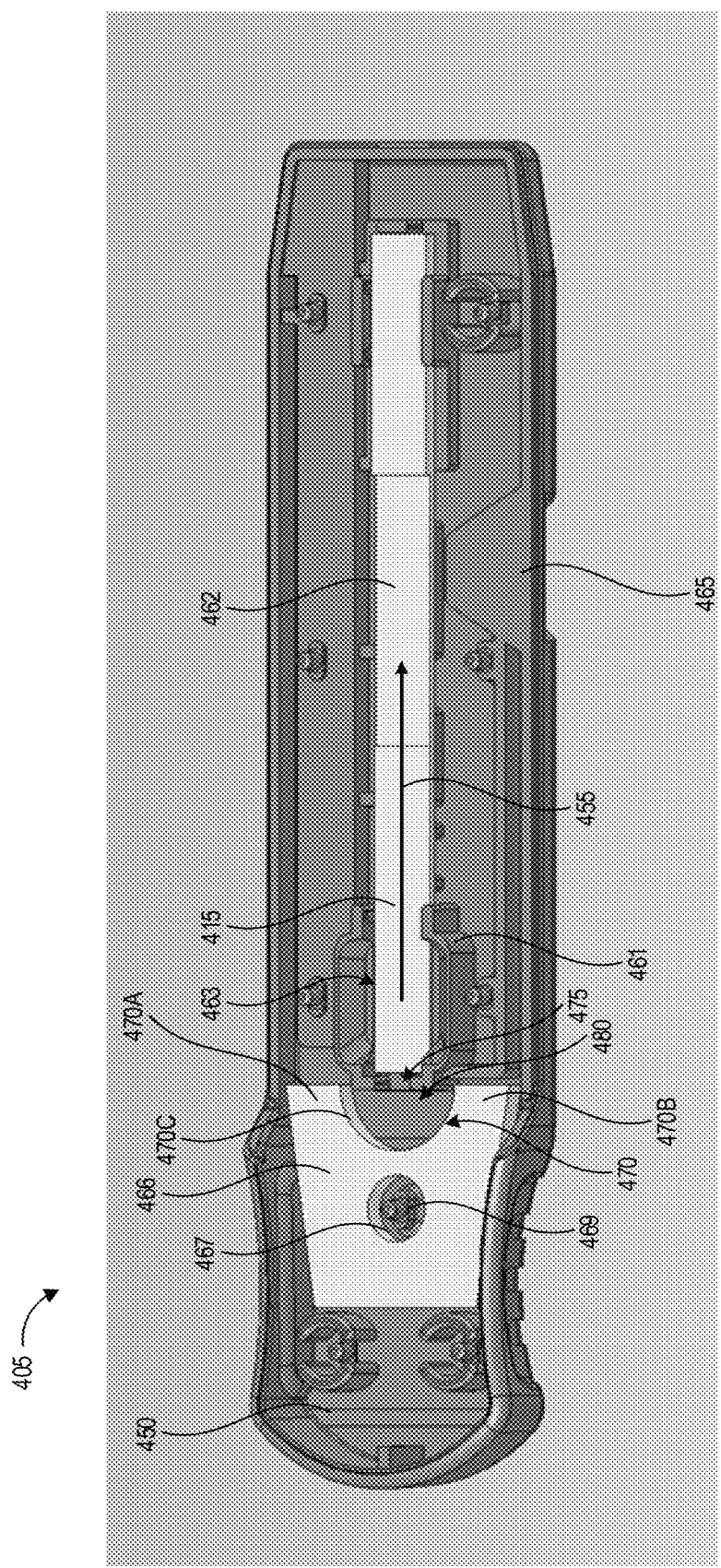

FIG. 4E illustrates a cut-away view showing interior features of an example of the assay cartridge 405. An assay test strip 463 including sample receiving zone 415 at a proximal end and analyte binding zone 462 at a distal end. The analyte binding zone 462 can be secured within a first region 461 of the cartridge housing 465. Analyte binding zone 462 can include multiple detection lines as discussed with reference to FIGS. 4A-4C. Capillary action can cause applied liquid to flow from the sample receiving zone 415 to the analyte binding zone 462 along a lateral flow direction 455. The first region 461 includes an exit aperture 475 through which any excess fluid overflowing backwards relative to the lateral flow direction 455 from the sample receiving zone 415 is directed. An overflow pad 466 can be secured in a second region 450 (e.g., within a grip portion of the cartridge 405) that is positioned upstream of the first region 461, where "upstream" refers to the second region 450 being positioned closer to the proximal end of the test strip 463 than the the first region 461 along the lateral flow direction 455. For example, the overflow pad 466 can be secured via an aperture 467 and corresponding protrusion 469 on the cartridge housing 465 or by other suitable fixing features (e.g. clips, adhesives, and/or clamping together of two halves of the cartridge housing 465).

The overflow pad 466 can be made from an absorbent material, and can operate to absorb any excess fluid that flows out of the assay test strip 463, thereby preventing such fluid from escaping the housing 465 and protecting the user from contacting potentially hazardous fluid. For example, if the user drips too much fluid onto the sample receiving zone 415, some fluid can run out of the exit aperture 475 and out of the assay strip 463 into the cartridge interior. This fluid can then leak out of the cartridge, spreading any contamination present in the fluid. Embodiments of assay cartridge 405 that include overflow pad 466 can collect such fluid and contain it within the cartridge 405. If the overflow pad 466 is placed too close to the assay strip 463 (e.g., in contact with the assay test strip 463) then the overflow pad 466 may reverse the intended lateral flow direction by drawing out fluid that would flow along the assay test strip 463 from the sample receiving zone 415 to the analyte binding zone 462 during normal operation. Embodiments of assay cartridge 405 allow at least some fluid to flow away from the overflow pad 466 to the analyte binding zone 462 for development of test results. Accordingly, in some embodiments, the overflow pad 466 can be spaced apart from the proximal end of the assay test strip 463 by a gap 480.

The overflow pad 466 can also be shaped to have a contoured end 470 that faces the assay test strip 463, for example shaped as two prongs 470A, 470B and a curved edge 470C forming a negative space between the two prongs 470A, 470B as in the illustrated example. The curved edge 470C wraps around the exit aperture 475 to block fluid paths of excess fluid traveling out of the exit aperture 475. Thus, the design of the contoured end 470 encapsulates the space around the exit aperture 475, thereby absorbing any excess fluid that travels out of the exit aperture 475 so that it cannot escape from the cartridge 405. At the same time, the curved edge 470C keeps the overflow pad 466 far enough away from the proximal end of the assay test strip 463 to ensure that the overflow pad 466 does not wick fluid out of the assay test strip 463.

Figure 5:
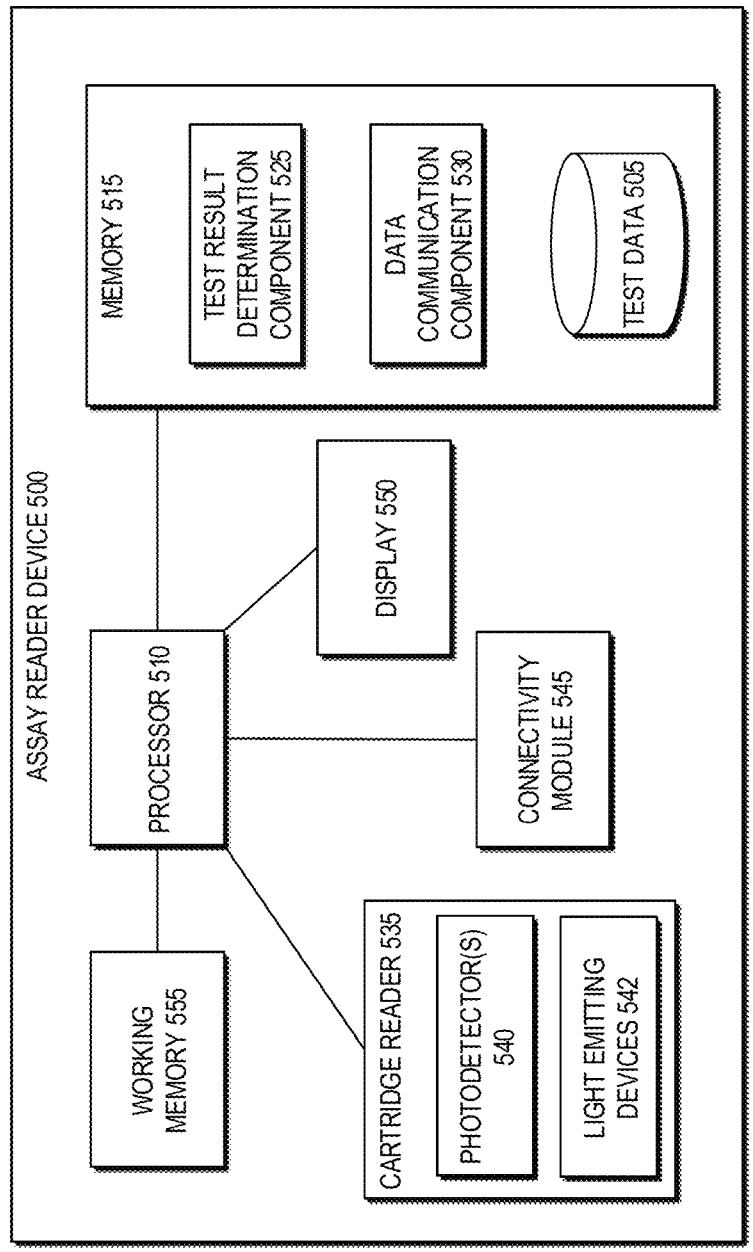
FIG. 5 depicts a high level schematic block diagram of an example testing device.

FIG. 5 illustrates a schematic block diagram of one possible embodiment of components of an example assay reader device 500. The components can include a processor 510 linked to and in electronic communication with a memory 515, working memory 555, cartridge reader 535, connectivity module interface 545, and display 550.

Connectivity module 545 can include electronic components for wired and/or wireless communications with other devices. For example, connectivity module 545 can include a wireless connection such as a cellular modem, satellite connection, or Wi-Fi, or via a wired connection. Thus, with connectivity module 545 the assay reader device can be capable of sending or uploading data to a remote repository via a network and/or receiving data from the remote repository. As such, the test data of such assay reader devices can be stored and analyzed, alone or in the aggregate, by remote devices or personnel. A module having a cellular or satellite modem provides a built-in mechanism for accessing publicly available networks, such as telephone or cellular networks, to enable direct communication by the assay reader device with network elements or other testing devices to enable electronic test result transmission, storage, analysis and/or dissemination without requiring separate intervention or action by the user of the device. In some embodiments connectivity module 545 can provide connection to a cloud database, for example a server-based data store. The cloud based connectivity module can enable ubiquitous connectivity of assay reader devices without the need for a localized network infrastructure.

The cartridge reader 535 can include one or more photodetectors 540 for reading an assay including multiple test regions held in an inserted cartridge and optionally any information on the inserted cartridge, for example a barcode printed on the cartridge, and one or more light emitting devices 542 for illuminating the inserted cartridge at one or more wavelengths of light. In some embodiments the cartridge reader 535 can additionally include light emitting devices 543 (e.g., LEDs) positioned to illuminate the test regions. The cartridge reader 535 can send data from the one or more photodetectors to the processor 510 for analysis of the data representing optical changes in the assay to determine a test result of the assay. The cartridge reader 535 can further send signals/data from the one or more photodetectors representing the cartridge for use in determining which one of a number of automated operating processes to implement for analyzing the assay and/or analyzing the signals/data obtained of the assay. The photodetector(s) 540 can be any device suitable for generating electric signals representing incident light, for example a PIN diode or array of PIN diodes, a charge-coupled device (CCD), or a complementary metal oxide semiconductor (CMOS) sensor, to name a few examples. The cartridge reader 535 can also include a component for detecting cartridge insertion, for example a mechanical button, electromagnetic sensor, or other cartridge sensing device. An indication from this component can instruct the processor 510 to begin an automated assay reading process without any further input or instructions from the user of the device 500.

Processor 510 can be configured to perform various processing operations on data received from the cartridge reader 535 (for example, optical saturation data or imaging data) and/or connectivity module interface 545 in order to determine and store test result data, as will be described in more detail below. Processor 510 may be a general purpose processing unit implementing assay analysis functions or a processor specially designed for assay detection and analysis applications. The processor 510 can be a microcontroller, a microprocessor, or ASIC, to name a few examples, and may comprise a plurality of processors in some embodiments.

As shown, the processor 510 is connected to a memory 515 and a working memory 555. In the illustrated embodiment, the memory 515 stores test result determination component 525, data communication component 530, and test data repository 505. These modules include instructions that configure the processor 510 of device 500 to perform various module interfacing, signal processing, and device management tasks. Working memory 555 may be used by processor 510 to store a working set of processor instructions contained in the modules of memory 515. Alternatively, working memory 555 may also be used by processor 510 to store dynamic data created during the operation of device 500.

As mentioned above, the processor 510 may be configured by several modules stored in the memory 515. The test result determination component 525 can include instructions that call subroutines to configure the processor 510 to analyze assay optical signals/data received from the photodetector(s) 540 to determine a result of the assay, including analyzing a number of different test zones and determining a final result based on the different test zones. In some implementations the subroutines can configure the processor 510 also to determine a probability of the test result and optionally of alternate possible test results. For example, the processor can compare detected optical signals/data to a number of templates or pre-identified patterns to determine the test result. In some implementations, test result determination component 525 can configure the processor 510 to implement adaptive read processes on optical signals/data from the photodetector(s) 540 to improve specificity of test results and to reduce false-positive results by compensating for background and non-specific binding.

The data communication component 530 can determine whether a network connection is available and can manage transmission of test result data to determined personnel and/or remote databases. If the device 500 is not presently part of a network, the data communication component 530 can cause local storage of test results and associated information in the test data repository 505. In some case, the device 500 can be instructed to or automatically transmit the stored test results upon connection to a network. If a local wired or wireless connection is established between the device 500 and another computing device, for example a hospital, clinician, or patient computer, the data communication component 530 can prompt a user of the device 500 to provide a password in order to access the data in the repository 505.

The processor 510 can be configured to control the display 550 to display captured optical signals/data, imaged barcodes, test results, and user instructions, for example. The display 550 may include a panel display, for example, a LCD screen, LED screen, or other display technologies, and may implement touch sensitive technologies.

Processor 510 may write data to data repository 505, for example data representing optical signals detected from assays, instructions or information associated with detected assays, and determined test results. While data repository 505 is represented graphically as a traditional disk device, those with skill in the art would understand that the data repository 505 may be configured as any storage media device. For example, data repository 505 may include a disk drive, such as a hard disk drive, optical disk drive or magneto-optical disk drive, or a solid state memory such as a FLASH memory, RAM, ROM, and/or EEPROM. The data repository 505 can also include multiple memory units, and any one of the memory units may be configured to be within the assay reader device 500, or may be external to the device 500. For example, the data repository 505 may include a ROM memory containing system program instructions stored within the assay reader device 500. The data repository 505 may also include memory cards or high speed memories configured to store captured optical signals and/or images which may be removable from the device 500.

Although FIG. 5 depicts a device having separate components to include a processor, cartridge reader, connectivity module, and memory, one skilled in the art would recognize that these separate components may be combined in a variety of ways to achieve particular design objectives. For example, in an alternative embodiment, the memory components may be combined with processor components to save cost and improve performance.

Additionally, although FIG. 5 illustrates a number of memory components, including memory 515 comprising several modules and a separate memory 555 comprising a working memory, one of skill in the art would recognize several embodiments utilizing different memory architectures. For example, a design may utilize ROM or static RAM memory, internal memory of the device, and/or an external memory (e.g., a USB drive) for the storage of processor instructions implementing the modules contained in memory 515. The processor instructions may be loaded into RAM to facilitate execution by the processor 510. For example, working memory 555 may comprise RAM memory, with instructions loaded into working memory 555 before execution by the processor 510.

The device 500 can further include other components not illustrated, for example one or more input devices, one or more connection/data transfer ports, one or more additional output devices such as an audio output device, and a power source/interface. The device may additionally include a transmitter and a receiver, for example as part of the connectivity module 545. The transmitter and receiver may be jointly referred to as a transceiver. The transceiver may be coupled to one or more antennas for transmitting and/or receiving wireless signals.

Overview of Example Tuned Assay Reading Techniques

Figure 6:
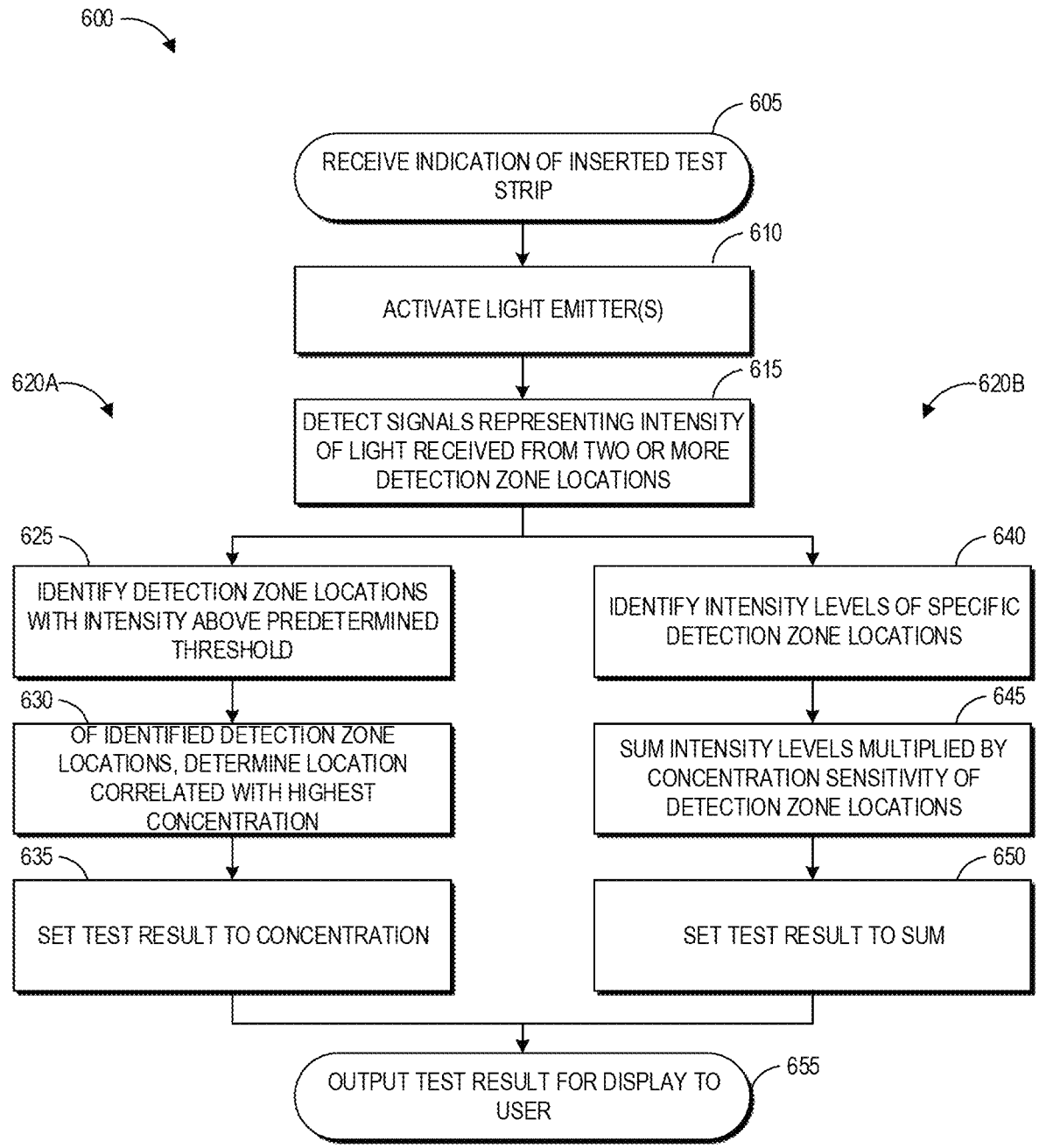
FIG. 6 illustrates an example process for reading a tuned assay test strip as described herein.

FIG. 6 illustrates an example process 600 for reading a tuned assay test strip as described herein. The process 600 can be implemented by the reader devices 300, 500 in some embodiments using test strips 100, 400A, or 400B. The process 600 can involve differentiating between various possible levels of saturation of multiple detection zones of a test strip, correlating the specific detected saturation level with a concentration level of a desired analyte, and determining the total concentration based on aggregate analysis of the correlated concentration levels of the multiple detection zones. In some embodiments, this requires optical sensitivity that is not achievable by a human viewing the test strip, as well as knowledge of the specific correlations between saturation levels and concentration levels for each of the multiple detection zones. As such, the hardware and programming of the reader device 300, 500 provides an estimate of the concentration of contaminant in the sample at a level of precision that a human viewing the test strip would be unable to provide. Some embodiments of the process 600 can be used to determine concentrations of anti-neoplastic drugs, such as but not limited to Methotrexate and Doxorubicin.

At block 605, the reader device can receive an indication that a test strip is inserted. The indication can be mechanical in some embodiments, for example depression of a switch or button by an inserted cartridge. In some embodiments, a user can provide the indication by pressing a button on the reader device. In some embodiments, the reader device can optically detect the inserted test strip.

At block 610, the reader device can optionally activate one or more light emitting devices to illuminate the detection zones of the inserted test strip. The reader device can activate the light emitting devices for the duration of detecting signals from the test strip.

At block 615 the reader device can detect signals representing intensity of light received from each of two or more detection zone locations. These can be the detection zones C1-C5 or D1-D5 described above, or similar detection zones tuned to different analyte concentrations and/or usable together to determine analyte concentration. For example, the reader device can collect light reflected from a detection zone via a photosensitive element and can convert the collected light into an electrical signal having a value corresponding to the saturation intensity of the detection zone. As described above, embodiments of the systems and methods described herein are not limited to this method of detection, and any suitable mechanism to detect changes in signals emanating from the detection zones can be implemented in the systems and methods described herein.

After block 615, the process 600 can move into one of two sub-processes 620A and 620B. Some embodiments can execute both sub-processes 620A, 620B in series or in parallel and can generate a final result based on the results of both sub-processes.

For sub-process 620A, process 600 transitions to block 625 to identify detection zone locations having signals corresponding to saturation intensities above a predetermined threshold. As described above, the saturation intensity of a detection zone can be in an inverse relationship with the concentration of analyte of interest in a sample applied to the test strip, and can therefore be tuned to saturate in the presence of analyte of interest at a particular concentration. For example, the reader device can be programmed to identify a detection zone as sufficiently saturated if the signal intensity indicates that the saturation of the test line was greater than or equal to a threshold percentage of full saturation (e.g., 50%, 75%, 90%, 95%, 100%, etc.).

In a first non-limiting example such as that illustrated above with reference to FIG. 4A, five detection zones tuned to different concentrations: 0.01 ng/cm$^2$, 0.1 ng/cm$^2$, 0.5 ng/cm$^2$, 1.0 ng/cm$^2$, and 1.5 ng/cm$^2$, respectively. In this first example, the detection zones are deemed to be sufficiently saturated at the same predetermined threshold percentage of full saturation, in this case 80% of maximum saturation for each of five detection zones. In this first example, the process 600 identifies at block 625 that the first, the second, and the third of the five detection zone locations have intensities above the 80% predetermined threshold when they have signals corresponding to saturation intensities of 80% or more of maximum saturation.

In a second non-limiting example such as that described above with reference to FIG. 4B, five detection zones are tuned to the same concentration 10 ng/cm$^2$. In this second example, the detection zones are deemed be sufficiently saturated at different predetermined threshold percentages. The first detection zone is deemed to be fully saturated at 95% of a maximum saturation for the first detection zone, the second detection zone is deemed to be fully saturated at 90% of a maximum saturation for the second detection zone, the third detection zone is deemed to be fully saturated at 85% of a maximum saturation for the third detection zone, the fourth detection zone is deemed to be fully saturated at 80% of a maximum saturation for the fourth detection zone, and the fifth detection zone is deemed to be fully saturated at 75% of a maximum saturation for the fifth detection zone. In this second example, the process identifies at block 625 that the first of the five detection zones has an intensity above the 95% predetermined threshold value for the first detection zone, the second of the five detection zones has an intensity above the 90% predetermined threshold value for the second detection zone, and the third, fourth, and fifth detection zones do not have intensities above their respective predetermined threshold values.

At block 630, the reader device can identify the sufficiently saturated detection zone located farthest along the lateral flow path and/or that is tuned to the highest concentration. As described above, this can be the sufficiently saturated detection zone located farthest along the lateral flow path.

In the first non-limiting example discussed above, the reader device can determine, of the identified sufficiently-saturated detection zone locations, the location correlated with the highest concentration. In this example, the reader device can determine that, of the first, second, and third detection zone locations identified in step 625, the third detection zone is located farthest along the lateral flow path and therefore corresponds to a highest concentration of 0.5 ng/cm$^2$.

In the second non-limiting example discussed above, the reader device can determine, of the identified sufficiently-saturated detection zone locations, the location correlated with the highest concentration. In this example, the reader device can determine the saturation level of the first detection zone is 97%, indicating a concentration of [10*0.97], or 9.7 ng/cm$^2$. The reader device can determine the saturation level of the second detection zone is 91%, indicating a concentration of [10*0.91], or 9.1 ng/cm$^2$. Accordingly, the reader device will determine that the location correlated with the highest concentration is the first detection zone (corresponding to a concentration of 9.7 ng/cm$^2$.

At block 635, the reader device can set the test result to the concentration level associated with the detection zone location identified at block 630. In the first non-limiting example discussed above, the reader device will set the test result to a concentration of 0.5 ng/cm$^2$, the concentration associated with the third detection zone identified at block 630. In the second non-limiting example discussed above, the reader device will set the test result to a concentration of 9.7 ng/cm$^2$, the concentration associated with the first detection zone identified at block 630. In some implementations, the reader device can additionally calculate a confidence value indicative of a level of confidence in the concentration reading as described above.

At block 655, the reader device can output the test result for display to a user, for example via display 315, 550. A confidence value can also be displayed at block 655 in some examples.

For sub-process 620B, process 600 transitions to block 640 to identify the signal intensity levels corresponding to specific detection zone locations. This can be performed for each detection zone location in some implementations by generating an average intensity of a number of pixels corresponding to a detection zone.

At block 645, the reader device can multiply the intensity levels by the corresponding concentration to which the respective detection zone is tuned. The reader device can further sum these values to generate a concentration level based on the saturation and concentration levels of all detection zones.

In the first non-limiting example discussed above, the reader device can determine the saturation level of the five detection zones at step 640. In this example, the reader device determines the saturation level of the first detection zone is 95%, indicating a concentration of [0.01*0.95], or 0.0095 ng/cm$^2$. The reader device can determine the saturation level of the second detection zone is 92%, indicating a concentration of [0.1*0.92], or 0.092 ng/cm$^2$. The reader device can determine the saturation level of the third detection zone is 83% percent, indicating a concentration of [0.5*0.83], or 0.415 ng/cm$^2$. At step 645, the reader device can sum the product of saturation level and concentration level for the first, second, and third detection zones. In this example, the reader device can sum 0.0095 ng/cm$^2$ (first detection zone), 0.092 ng/cm$^2$ (second detection zone), and 0.415 ng/cm$^2$ (third detection zone) to obtain a sum of 0.5165 ng/cm$^2$.

In the second non-limiting example discussed above, the reader device can determine the saturation level of the first detection zone is 97%, indicating a concentration of [10*0.97], or 9.7 ng/cm$^2$. The reader device can determine the saturation level of the second detection zone is 91%, indicating a concentration of [10*0.91], or 9.1 ng/cm$^2$. At step 645, the reader device can sum the product of saturation level and concentration level for the first and second detection zones. In this example, the reader device can sum 9.7 ng/cm$^2$ (first detection zone) and 9.1 ng/cm$^2$ (second detection zone) to obtain a sum of 18.8 ng/cm$^2$.

At block 650, the reader device can set the test result to the sum. In the first non-limiting example describes above, the reader device can set the test result to the sum of 0.5165 ng/cm². In the second non-limiting example describes above, the reader device can set the test result to the sum of 18.8 ng/cm². In some implementations, the reader device can additionally calculate a confidence value indicative of a level of confidence in the concentration reading, as described above.

At block 655, the reader device can output the test result for display to a user, for example via display 315, 550. A confidence value can also be displayed at block 655 in some examples. In cases where the reader device executes sub-process 620A and sub-process 620B in series or in parallel, the reader device can output a final result based on the results of both sub-processes. For example, the reader device can output an average of the results of both sub-processes, output the higher of the two results of the sub-processes, or output the lower of the two results of the sub-processes.

Overview of Example Feedback and Indications

Binary classifiers can suffer from high probability of misclassification near cutoff thresholds. For some systems the zone of uncertainty is small and is simply ignored. For some systems, such as assays, the zone of uncertainty may be quite large, for example as much as 50% of the threshold value. The disclosed reader devices can analyze the size of the zone of uncertainty to provide a more realistic or accurate test result when measured values of detection zone saturations fall within the zone of uncertainty. This can help to prevent the confusion that follows when repeated measurements of the same potentially contaminated surface "flip-flop" between yes and no. The disclosed techniques also gives the facility managers potentially time to react to a zone that is transitioning into hazardous contamination, where test results may indicate that the zone is not all the way "green" (e.g., uncontaminated) and not alarmingly red (e.g., dangerously contaminated) yet. Although a zone in such a transition period might not be too harmful to humans, the disclosed techniques can beneficially enable preventative action to be taken so that the zone can be decontaminated before it becomes a more harmful environment. The healthcare facility testing the zone could also initiate a higher sampling frequency when something is in the transition zone to watch if its level of contamination drifts upward or downward.

The reader device according to the present disclosure can use a variety of thresholds to determine whether to label a test zone as green, red, or yellow. It will be appreciated that these colors are provided as one example and various indicators can be used to convey the contamination status of a tested zone. In one implementation, a reader device may allow individual users, pharmacies, hospitals, or laboratories to set the detection thresholds to a level of their choosing, for example based on their practice and tolerance of risk. The user may also be allowed to set the size of the zone of uncertainty according to their tolerance for rate of misclassification. Other reader devices can be pre-programmed with such thresholds and/or receive thresholds via a network connection, for example from health agencies or research groups with updated information on safe or tolerable levels of various hazardous drugs.

Figure 7A:
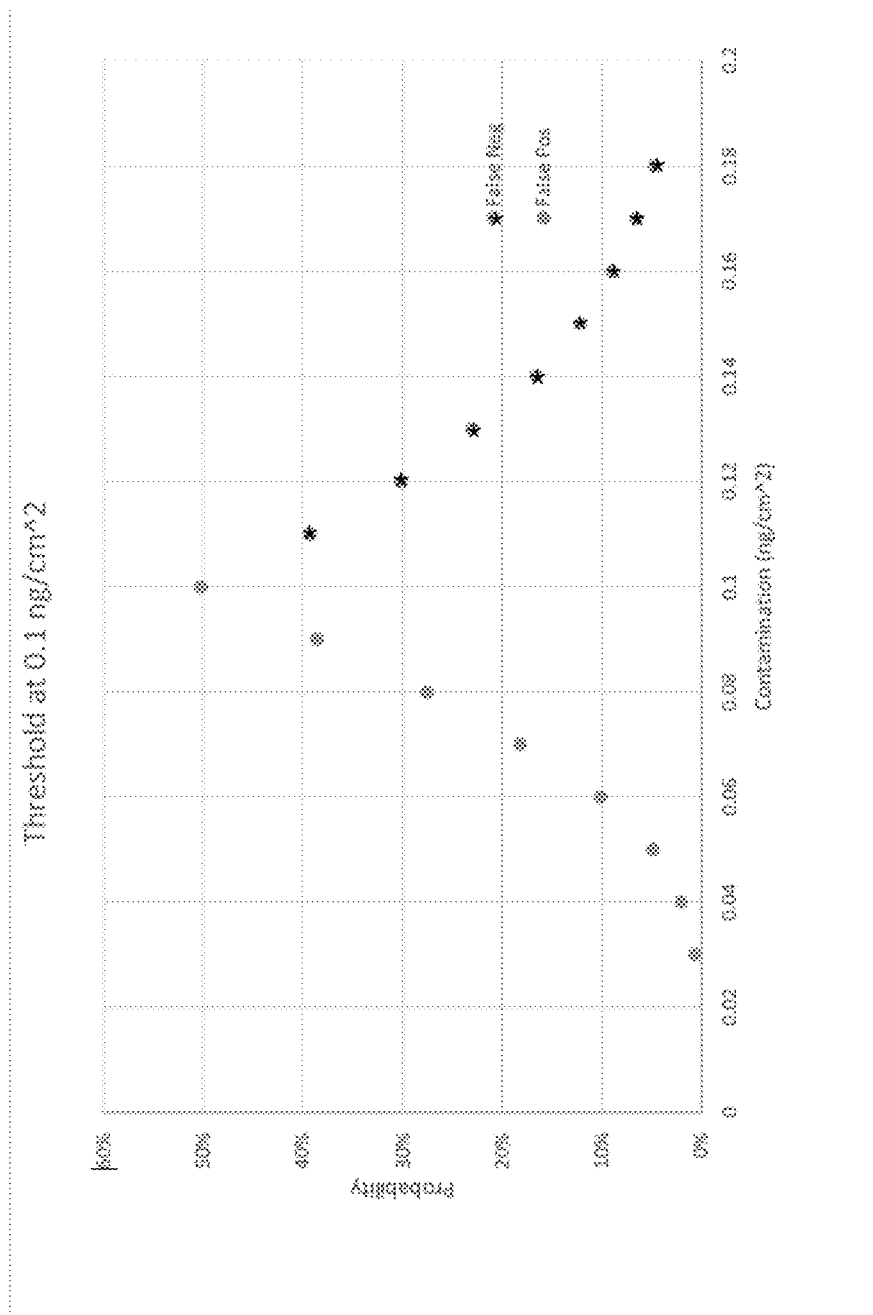
FIGS. 7A and 7B depict plots charting probability of various contamination levels.
Figure 7B:
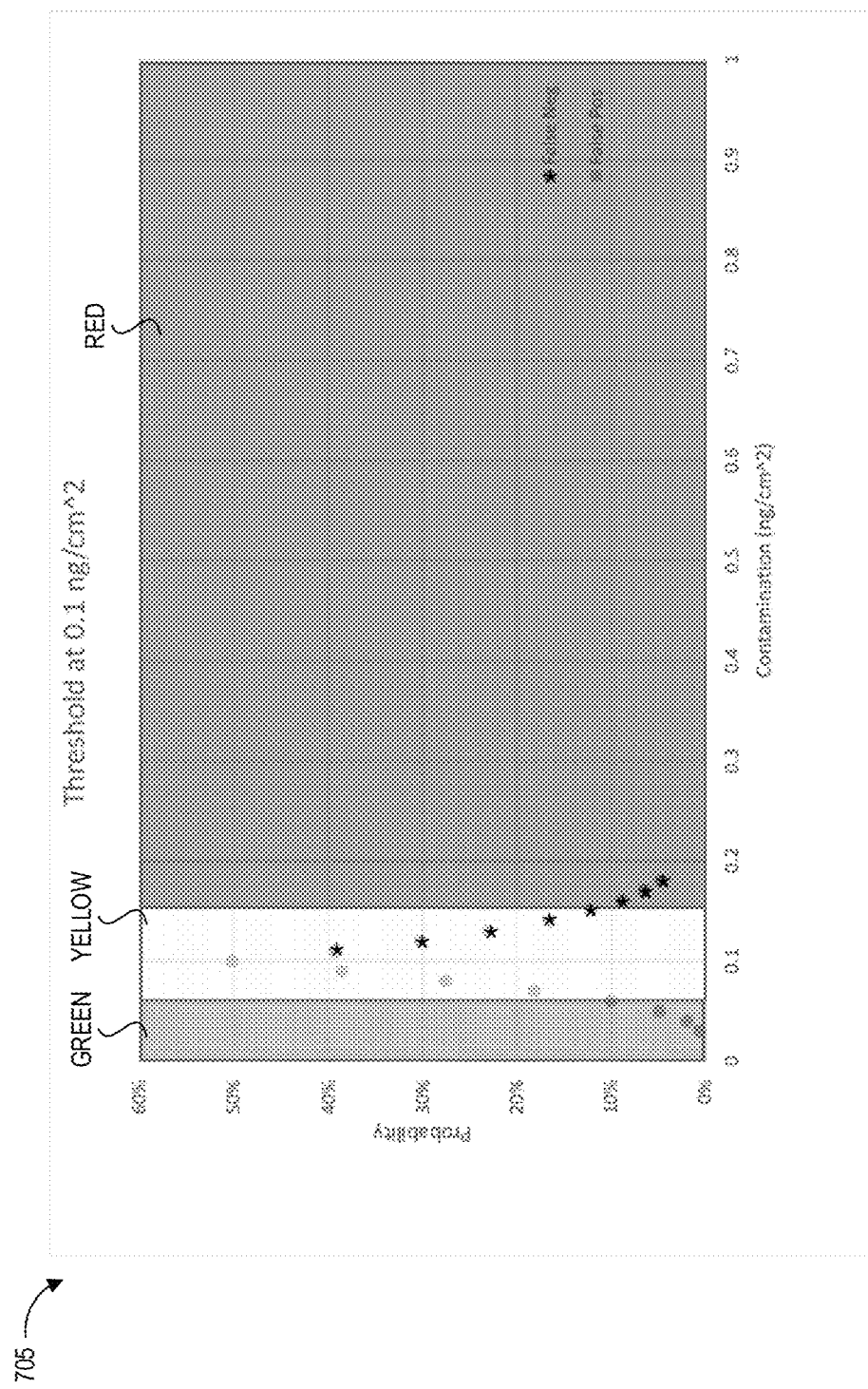

FIGS. 7A and 7B depict plots charting probability of various contamination levels. The plots of FIGS. 7A and 7B represent information that can be used by a reader device, for example reader devices 300, 500, to communicate a test result (e.g., concentration level and optionally confidence value) based on a probability of misclassification.

FIG. 7A depicts a plot 700 of a folded cumulative distribution function mapping contamination concentration versus probability, with a threshold set at 0.1 ng/cm². As indicated by the orange dots, the probability of generating a false positive result increases exponentially approaching the threshold of 0.1 ng/cm² from the direction of the minimum concentration (0 ng/cm²). As indicated by the blue dots, the probability of generating a false negative result decreases exponentially approaching the threshold of 0.1 ng/cm² from the direction of the maximum concentration (shown as 0.2 ng/cm²).

FIG. 7B depicts a plot 705 showing the same cumulative distribution function as FIG. 7A, but with the x-axis (contamination concentration) extended to 1 ng/cm². Further, the plot 705 is overlaid with bands of color—green from 0 ng/cm² to 0.05 ng/cm², yellow from 0.05 ng/cm² to 0.15 ng/cm², and red above 0.15 ng/cm². These colors represent colors or other indicators (textual warnings, auditory warnings) that can be presented to a user via the reader device with the determined test result. A color-based indication of assay result can be presented, for example, by changing the color of the text or background on display 315, 550, by activating a correspondingly colored LED or other light on the body of the reader device, or sent as part of a test result indication to a user's personal computing device. Thus, rather than simply reporting a yes (contaminated/red) or no (not contaminated/green), the reader device can output an indication along the lines of "maybe", "yellow", "transitioning" or "inconclusive", etc. when measured values are near a threshold and the probability of a misclassification is high.

One embodiment of a reader device suitable for displaying indications according to FIGS. 7A and 7B can be programmed to implement a method of Monte Carlo analysis to construct folded cumulative distribution functions in real time. In another implementation, probabilistic modeling of system behavior is used to construct the folded cumulative distribution functions for false positive and false negative values associated with a particular analyte of interest and testing methodology. The reader device can then be programmed to implement the folded cumulative distribution functions (sometimes referred to as a mountain plot as the false positives and false negative cumulative distribution functions converge at 50% probability at the decision threshold). The disclosed confidence indications can be used with assays having a plurality of detection zones, as described herein, or with assays having a single detection zone.

Overview of Additional Embodiments

In some embodiments, the disclosed test strips can be used with a system of multiple test strips and/or multiple buffer solutions to enhance dynamic range. For example, a kit may include a multiplexed test strip that has multiple detection zones each tuned to some low or lowest level of a different drug. To illustrate, a test strip could have a first detection zone that fully saturates at 0.01 ng/cm² of Methotrexate and a second detection zone that fully saturates at 0.01 ng/cm² Doxorubicin. Other examples can be tuned to other saturation levels and can include greater numbers of detection zones configured for saturation in response to the presence of other antineoplastic drugs.

If a signal is detected at this lowest level at one of the detection zones (or at multiple zones), the user can retrieve a second test strip specific to the detected drug, with the second test strip having an extended dynamic range as described herein. Thus, the kit may include a number of low-level multiplexed strips together with extended dynamic range strips that are each specific to one of the drugs of the multiplexed strip.

In another example, if a signal is detected at this lowest level at one of the detection zones (or at multiple zones), the user can iteratively dilute the buffer solution that was applied to the test strip a known amount and continue to use low-saturation test strips (such as the multiplexed test strip) until the test strip can measure the antineoplastic drug in the proper range. The total concentration can then be determined based on the dilution amount and the read concentration in order to produce the detected concentration, which the reader can translate to the total concentration for display to the user.

In a similar example, the kit can include a staged buffer solution system. The original fluid container can be expressed into a known volume, effectively diluting the concentration with an order of magnitude reduction in concentration. This can be repeated several times if necessary to obtain the relevant reading on the device.

In these last two examples, the reader device can be provided with an indication regarding the number of times the user diluted the sample. For example, the device can be told that the user diluted the sample four times, and thus would calculate the reading with the 4× (or 40× or 400×) dilution factor to give the user the proper reading based on the level of dilution. This can provide a volumetric solution to the disclosed enhanced dynamic range that can be used together with, or in place of, the assays described above with reference to FIGS. 4A-4C.

IMPLEMENTING SYSTEMS AND TERMINOLOGY

Implementations disclosed herein provide systems, methods and apparatus for detection of the presence and/or quantity of hazardous drugs. One skilled in the art will recognize that these embodiments may be implemented in hardware or a combination of hardware and software and/or firmware.

The assay reading functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like. The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. Thus, the present invention is not intended to be limited to the implementations shown herein but is to be accorded the widest scope consistent with the principles and novel features disclosed herein.

What is claimed is:
1. A system for detection of a hazardous contaminant, comprising:
  an assay test strip including:
    at least one material configured to wick a liquid sample containing the hazardous contaminant along a lateral flow path extending at least partway from a first end of the assay test strip to a second end of the assay test strip;

a conjugate release zone comprising a plurality of diffusively bound labeled particles configured to be transported along the lateral flow path with the liquid sample; and a plurality of detection zones positioned sequentially along the lateral flow path, each of the plurality of detection zones comprising a plurality of immobilized capture reagents tuned to fully saturate with the labeled particles at a specific concentration level of the hazardous contaminant, wherein each detection zone of the plurality of detection zones comprises different immobilized capture reagents or a different capture reagent loading concentration relative to at least one other detection zone, such that the plurality of detection zones are each tuned to a different one of a plurality of concentrations; and a reader device including:
a portion configured to receive the assay test strip;
a sensor positioned to receive light reflected from the plurality of detection zones and configured to generate signals representing an intensity of the received light; and
control electronics comprising at least one processor and memory storing computer-executable instructions that, when executed by the at least one processor, cause the control electronics to:
analyze the signals to identify a subset of the plurality of detection zones saturated above a predetermined threshold,
determine a concentration of the hazardous contaminant based on one of the subset of the plurality of detection zones, and
identify a value representing a level of confidence in accuracy of the determined concentration of the hazardous contaminant in the liquid sample.

2. The system of claim 1, wherein the computer-executable instructions further cause the control electronics to:
calculate, based on the signals, a saturation level of each of the plurality of detection zones;
access data representing the concentration level associated with each of the plurality of detection zones; and
calculate the concentration of the hazardous contaminant in the liquid sample based on the calculated saturation level and associated concentration level of each of the plurality of detection zones.

3. The system of claim 2, wherein the computer-executable instructions further cause the control electronics to:
for each of the plurality of detection zones, generate a concentration product value by multiplying the calculated saturation level by the associated concentration level; and
sum the concentration product values to calculate the concentration of the hazardous contaminant in the liquid sample.

4. The system of claim 1, wherein the plurality of detection zones are arranged along the lateral flow path in increasing order based on their tuned concentrations.

5. The system of claim 1, further comprising a cartridge housing the assay test strip.

6. The system of claim 5, wherein the assay test strip comprises a sample receiving zone at the first end, and wherein the cartridge comprises a fluid fitting positioned to provide the liquid sample to the sample receiving zone.

7. The system of claim 6, wherein the fluid fitting is configured to provide a fluid-tight seal with a corresponding fluid fitting on a collection container for transferring the liquid sample from the collection container to the assay test strip.

8. The system of claim 5, wherein the cartridge comprises a barcode readable by the reader device to identify a number, location, and corresponding tuned concentration of each of the plurality of detection zones.

9. The system of claim 8, wherein the computer-executable instructions further cause the control electronics to identify the number, location, and corresponding tuned concentration of each of the plurality of detection zones based on signals from a barcode scanner representing the barcode.

10. The system of claim 1, wherein the assay test strip comprises a competitive assay, and wherein each of the plurality of detection zones is configured to saturate in an inverse relationship with the concentration of the hazardous contaminant in the liquid sample.

11. The system of claim 1, wherein the assay test strip further comprises a sample receiving zone upstream of the conjugate release zone, and wherein the system further comprises a cartridge housing the assay test strip, the cartridge comprising a fluid fitting positioned to provide the liquid sample to the sample receiving zone.

12. The system of claim 11, wherein the plurality of detection zones are arranged along the lateral flow path in increasing order based on their tuned concentrations.

13. The system of claim 11, further comprising a control zone configured to saturate regardless of concentration level of the hazardous contaminant in the liquid sample.

14. The system of claim 11, wherein the assay test strip comprises a competitive assay.

15. The system of claim 1, wherein the computer executable instructions further cause the control electronics to:
identify a highest concentration, from among the subset of the plurality of concentrations associated with the subset of the plurality of detection zones.

16. The system of claim 15, wherein the computer-executable instructions further cause the control electronics to set the concentration of the hazardous contaminant in the liquid sample to the identified highest concentration associated with the subset of the plurality of concentrations.

17. The system of claim 1, further comprising a barcode scanner positioned to read a barcode on a cartridge housing the assay test strip.

18. The system of claim 17, wherein the computer-executable instructions further cause the control electronics to identify, based on signals from the barcode scanner representing a scanned barcode, a number, location, and corresponding tuned concentration of each of the plurality of detection zones.

19. The system of claim 1, wherein the value is based on a difference between the concentration of the hazardous contaminant in the liquid sample and a predetermined threshold.

20. The system of claim 1, further comprising a display configured to display information representing the determined concentration of the hazardous contaminant in the liquid sample, wherein the computer-executable instructions further cause the control electronics to cause output of a visual indication of the confidence value to the display.

* * * * *